US011400295B2

(12) United States Patent
Min et al.

(10) Patent No.: US 11,400,295 B2
(45) Date of Patent: Aug. 2, 2022

(54) TIME DOMAIN-BASED METHODS FOR HIS BUNDLE CAPTURE CLASSIFICATION

(71) Applicant: Pacesetter, Inc., Sylmar, CA (US)

(72) Inventors: Xiaoyi Min, Thousand Oaks, CA (US); Yun Qiao, Valencia, CA (US); Wenwen Li, San Jose, CA (US); Jan O. Mangual-Soto, Rho (IT); Luke C. McSpadden, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 29 days.

(21) Appl. No.: 16/867,215

(22) Filed: May 5, 2020

(65) Prior Publication Data

US 2020/0353266 A1    Nov. 12, 2020

Related U.S. Application Data

(60) Provisional application No. 62/844,623, filed on May 7, 2019.

(51) Int. Cl.
*A61N 1/362* (2006.01)
*A61N 1/368* (2006.01)
*A61N 1/39* (2006.01)
*A61N 1/05* (2006.01)
*A61N 1/37* (2006.01)

(52) U.S. Cl.
CPC ........... *A61N 1/3627* (2013.01); *A61N 1/059* (2013.01); *A61N 1/368* (2013.01); *A61N 1/371* (2013.01); *A61N 1/39622* (2017.08)

(58) Field of Classification Search
CPC .. A61N 1/3627; A61N 1/39622; A61N 1/059; A61N 1/368; A61N 1/371
See application file for complete search history.

(56) References Cited

U.S. PATENT DOCUMENTS

| 5,718,720 A | * | 2/1998 | Prutchi | A61N 1/3712 607/28 |
| 2012/0239106 A1 | * | 9/2012 | Maskara | A61N 1/371 607/28 |
| 2019/0134405 A1 | * | 5/2019 | Sheldon | A61B 5/4836 |

* cited by examiner

*Primary Examiner* — William J Levicky
*Assistant Examiner* — Michael A Rizzuto
(74) *Attorney, Agent, or Firm* — The Small Patent Law Group LLC; Dean D. Small

(57) ABSTRACT

Systems and methods for His bundle pacing and classifying response to pacing impulses include applying, using a pulse generator, an impulse through a stimulating electrode to induce a response from a patient heart. A response to the impulse is measured using at least one sensing electrode and time-domain based characteristics of the response are analyzed to determine whether His bundle capture has occurred and, if so, what type of capture has occurred.

16 Claims, 17 Drawing Sheets

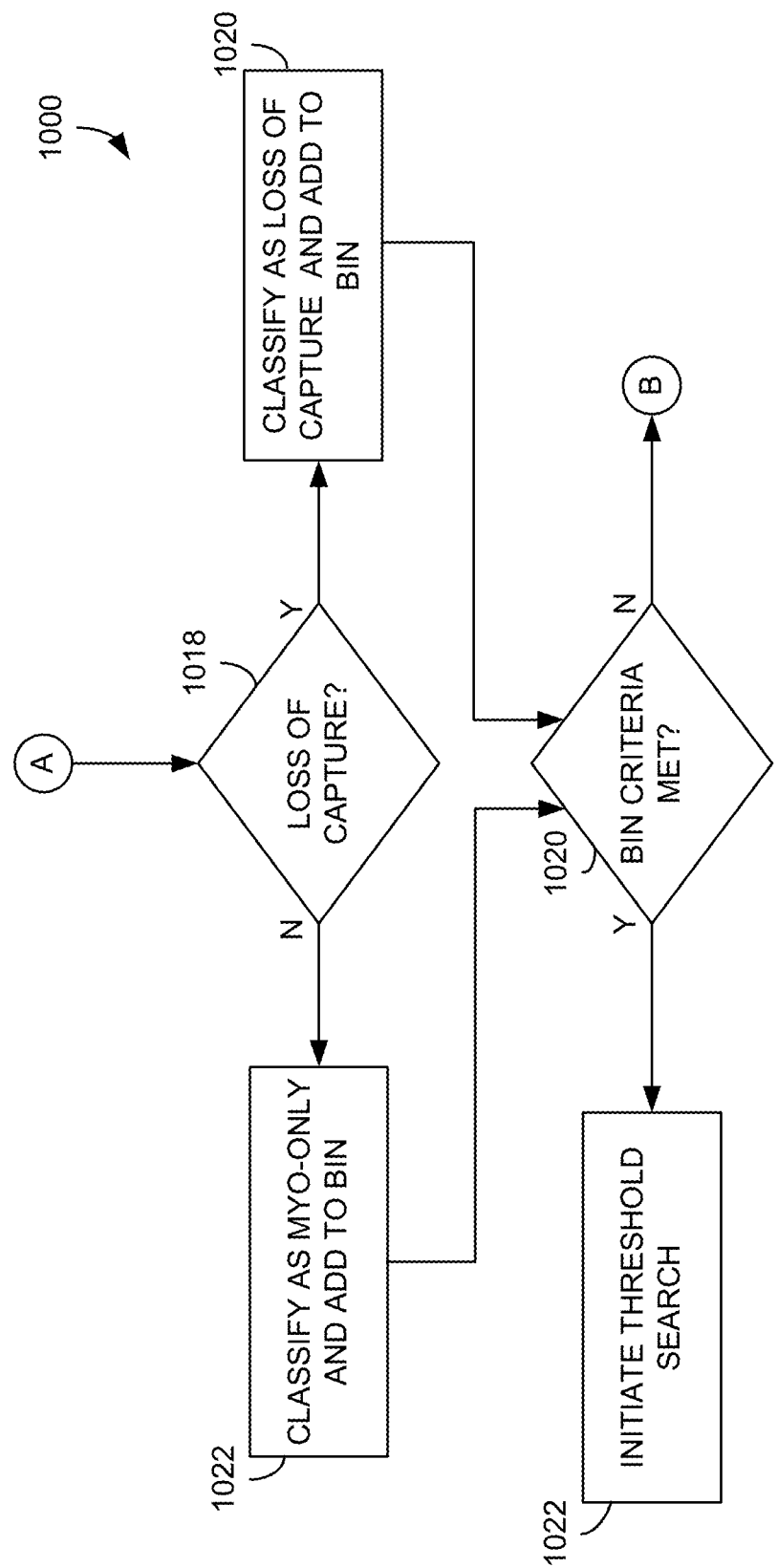

TIME DOMAIN-BASED METHODS FOR HIS BUNDLE CAPTURE CLASSIFICATION

CROSS-REFERENCE TO RELATED APPLICATIONS

This application claims the benefit of U.S. Provisional Application No. 62/844,623 filed May 7, 2019, which is hereby incorporated by reference in its entirety.

FIELD

This disclosure relates generally to implantable cardiac stimulating devices. More specifically, the present disclosure is directed to a cardiac stimulation device that includes a lead for His bundle pacing and that include logic for automatically classifying responses of the heart to application of pacing impulses to the His bundle.

BACKGROUND

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of His (also referred to as the His bundle), the left and right bundle branches, and the Purkinje fibers, causing depolarization and resulting contraction of the ventricular chamber. The depolarization of the interventricular septum and ventricles is generally referred to as a QRS complex and is observed by measuring electrical activity of the heart, such as by recording an electrocardiogram or electrogram.

The His bundle is a narrow cluster of cardiac muscle fibers that passes electrical impulses from the AV node to the interventricular septum. It is anatomically located adjacent to the annulus of the tricuspid valve, inferior to or within the membranous septum. During normal functioning of the heart, the delay between excitation of the His bundle and a subsequent depolarization of the ventricles in response to the excitation is generally on the order of approximately 30-50 milliseconds (ms) and the resulting QRS complex generally has a duration of approximately 70-100 ms.

Disruption of the natural pacemaking and conduction system of the heart as a result of aging or disease can be successfully treated by artificial cardiac pacing using implantable cardiac stimulation devices, including pacemakers and implantable defibrillators. Such devices deliver rhythmic electrical impulses at particular energies and rates or provide other anti-arrhythmia therapies to the heart via electrodes implanted in contact with the heart tissue. To the extent the electrical impulses are sufficient to induce depolarization of the associated heart tissue, the heart tissue is said to be captured. The minimum electrical impulse energy resulting in capture is generally referred to as the capture threshold for the heart tissue.

In the majority of individuals, the most effective heartbeat is triggered by the patient's own natural pacing physiology. Implantable cardiac stimulation devices are intended to fill in when the natural pacing functionality of the patient's heart fails or acts inefficiently (such as in cases of sinus arrest and symptomatic bradycardia, respectively) or when the heart's conduction system fails or acts inefficiently (such as in cases of third-degree and second-degree (i.e., Mobitz II) AV blocks, respectively). In a large number of heart failure patients, natural conduction through the AV node and the His bundle are intact and disruption of ventricular rhythm is the result of conduction disorders residing in the left and/or right bundle branches.

Dilatation of the heart due to congestive heart failure (CHF) has been associated with delayed conduction through the ventricles. This delayed conduction leads to reduced hemodynamic efficiency of the failing heart because of the resulting poor synchronization of the heart chambers.

Direct stimulation of the His bundle has been found to provide hemodynamic improvement for various patients including those suffering from dilated cardiomyopathy but having otherwise normal ventricular activation. Other examples of patients that may benefit from direct stimulation of the His bundle include those with atrioventricular junction (AVJ) ablation or third-degree AV block, which may require permanent ventricular pacing. Accordingly, the natural conduction system, when intact, can provide hemodynamically optimal depolarization timing of the heart chambers.

Among other things, a cardiac stimulation system is needed that is capable of identifying electrical pulses for inducing His bundle capture and self-configuring output settings of the cardiac stimulation system to output such electrical pulses. To improve efficiency and operational life of the cardiac stimulation device, it would be further desirable that the cardiac stimulation system also identify the minimum power and rate necessary to induce His bundle capture and subsequent ventricular depolarization.

To facilitate such functionality, such cardiac stimulation systems should also be capable of readily classifying responses of the patient's heart to the application of pacing impulses. More specifically, such cardiac stimulation systems should be capable of applying a pacing impulse, measuring the resulting response of the patient heart to the applied impulse, and classifying the response according to the cardiac tissue captured by the impulse and, in particular, whether the response indicates capture of the His bundle.

BRIEF SUMMARY OF THE DISCLOSURE

In one aspect of the present disclosure, a method of pacing a His bundle of a patient heart using a stimulation system is provided. The stimulation system includes a processor, a memory, a pulse generator, a stimulating electrode in proximity to the His bundle, and at least one sensing electrode adapted to sense electrical activity of the patient heart. The method includes applying, using the pulse generator, an impulse through the stimulating electrode to induce a response from the patient heart and measuring, using the sensing electrode, a response of the patient heart to application of the impulse. The method further includes analyzing a first set of time-domain characteristics of the response using the processor to determine whether the impulse resulted in capture of the His bundle.

In certain implementations, the first set of time-domain characteristics includes, without limitation, at least one of a morphology of the response; a time between application of the impulse and onset of the response; a time between application of the impulse and a peak of the response; a time between application of the impulse and a unipolar maximum slope of the response; a width of the response; an amplitude of the response; an integral of the response; a peak-to-peak slope of the response; or a peak-to-peak time of the response.

In other implementations, analyzing the first set of time-domain characteristics is to determine whether the impulse resulted in selective capture of the His bundle. In such implementations, the first set of time-domain characteristics includes the time delay between application of the impulse and the unipolar maximum slope of the response and determining whether the impulse resulted in selective capture includes determining whether the time delay exceeds about 70 ms.

In another implementation, analyzing the first set of time-domain characteristics is to determine whether the impulse resulted in selective capture of the His bundle. When the first set of time-domain characteristics does not indicate selective capture, the method further includes analyzing a second set of time-domain characteristics of the response using the processor, the second set of time-domain characteristics to determine whether the impulse resulted in non-selective capture. In such implementations, the second set of time-domain characteristics may include, without limitation, at least one of a morphology of the response; a time between application of the impulse and onset of the response; a time between application of the impulse and a peak of the response; a time between application of the impulse and a unipolar maximum slope of the response; a width of the response; an amplitude of the response; an integral of the response; a peak-to-peak slope of the response; a peak-to-peak time of the response; a time delay between application of the impulse and a last peak of the response; or a time delay between application of the impulse and an end of a peak slope of the response. In one particular implementation, the second set of time-domain characteristics includes the peak-to-peak time interval and determining whether the impulse resulted in non-selective capture includes determining whether the peak-to-peak interval exceeds about 60 ms.

In another specific implementation, the second set of time-domain characteristics includes the time delay between application of the impulse and the last peak of the response and determining whether the impulse resulted in non-selective capture includes determining whether the time delay between application of the impulse and the last peak of the response exceeds about 150 ms.

In still another specific implementation, the second set of time-domain characteristics includes the time delay between application of the impulse and the end of the peak slope of the response and determining whether the impulse resulted in non-selective capture include determining whether the time delay between application of the impulse and the end of the peak slope of the response exceeds about 150 ms.

In certain implementations, in response to determining the impulse did not result in non-selective capture, classifying the response as one of myocardium-only capture or loss of capture. In such implementations, the method may further include logging each occurrence of at myocardium-only capture or loss of capture in a log stored in the memory and initiating a capture threshold search in response to the log reaching a predetermined number of entries.

In another implementation, the method further includes applying one or more filters to the response, the one or more filters configured to one of stop or pass frequencies associated with a capture type, wherein analyzing the first set of time-domain characteristics of the response using the processor includes analyzing the response after applying the one or more filters.

In another aspect of the present disclosure, a cardiac stimulation system adapted to deliver impulses for pacing a His bundle of a patient heart using a stimulation electrode and to sense response characteristics of the His bundle and myocardium of the patient heart using one or more sensing electrodes in response to impulses delivered by the stimulation electrode. The stimulation system includes a pulse generator adapted to generate electrical impulses for pacing the His bundle, a processor communicatively coupled to the pulse generator and adapted to receive response characteristics from the one or more sensing electrodes, and a memory communicatively coupled to the processor. The memory includes instructions executable by the processor that, when executed by the processor, cause the processor to apply, using the pulse generator, an impulse through the stimulating electrode to induce a response from the patient heart and measure, using the sensing electrode, a response of the patient heart to application of the impulse. The instructions further cause the processor to analyze a first set of time-domain characteristics of the response, the first set of time-domain characteristics selected to determine whether the impulse resulted in capture of the His bundle.

In certain implementations, the first set of time-domain characteristics is to determine whether the impulse resulted in selective capture and includes at least one of a morphology of the response, or a time delay between applications of the impulse a unipolar maximum slope of the response.

In other implementations, the first set of time-domain characteristics is to determine whether the impulse resulted in selective capture. In response to determining the impulse did not result in selective capture, the instructions further cause the processor to analyze a second set of time-domain characteristics of the response to distinguish between non-selective capture and myocardium-only capture, the second set of characteristics including a peak-to-peak time interval. The instructions further cause the processor to determine that the impulse resulted in myocardium-only capture when the peak-to-peak interval exceeds about 60 ms and in non-selective capture when the peak-to-peak interval is below about 60 ms.

In still other implementations, the first set of time-domain characteristics is also to determine whether the impulse resulted in selective capture. In response to determining the impulse did not result in selective capture, the instructions further cause the processor to analyze a second set of time-domain characteristics of the response to distinguish between non-selective capture and myocardium-only capture, the second set of characteristics including a time delay between application of the impulse and a last peak of the response. In such implementations, the instructions may further cause the processor to determine that the impulse resulted in myocardium-only capture when the time delay exceeds about 150 ms and in non-selective capture when the peak-to-peak interval is below about 150 ms.

In yet other implementations, the first set of time-domain characteristics is to determine whether the impulse resulted in selective capture. In response to determining the impulse did not result in selective capture, the instructions further cause the processor to analyze a second set of time-domain characteristics of the response to distinguish between non-selective capture and myocardium-only capture, the second set of characteristics includes a time delay between application of the impulse and an end of a peak slope of the response. In such implementations, the instructions may further cause the processor to determine that the impulse resulted in myocardium-only capture when the time delay exceeds about 150 ms and in non-selective capture when the peak-to-peak interval is below about 150 ms.

In another aspect of the present disclosure, a method of pacing a His bundle of a patient heart using a stimulation system is provided. The stimulation system includes a processor, a memory, a pulse generator, a stimulating electrode in proximity to the His bundle, and at least one sensing electrode adapted to sense electrical activity of the patient heart. The method includes applying, using the pulse generator, an impulse through the stimulating electrode to induce a response from the patient heart and measuring, using the sensing electrode, a response of the patient heart to application of the impulse. The method further includes analyzing a first set of time-domain characteristics of the response using the processor to determine whether the impulse resulted in selective capture, and, in response to determining the impulse did not result in selective capture, analyzing a second set of time-domain characteristics of the response using the processor to determine whether the impulse resulted in one of non-selective capture or myocardium-only capture.

In certain implementations, wherein analyzing the first set of time-domain characteristics of the response further includes applying one or more filters configured to one of stop or pass frequencies indicative of selective capture.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

FIGS. 10A and 10B are a flow chart illustrating a method for identifying capture types by filtering responses to pacing impulses.

DETAILED DESCRIPTION

Figure 1:
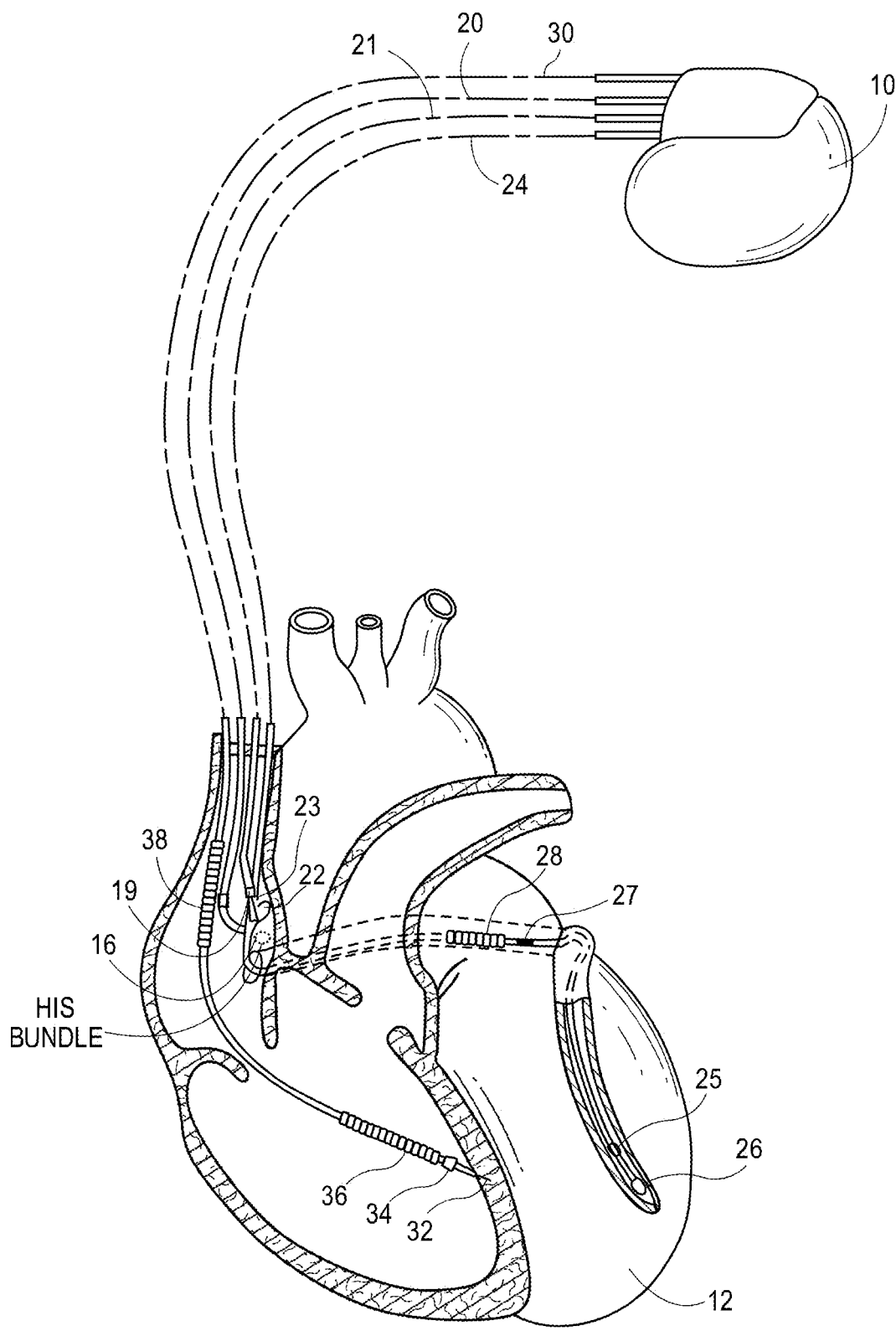
FIG. 1 is a simplified, partly cutaway view illustrating an implantable stimulation device in electrical communication with having multiple leads, including a His Bundle lead, implanted into a patient's heart for delivering multi-chamber stimulation and shock therapy.

The present disclosure is directed to various aspects of stimulation systems and corresponding methods related to His bundle pacing. Among other things, the present disclosure provides methods and systems for automatic classification of capture events in response to application of pacing impulses. Aspects of the present disclosure may be implemented in any suitable stimulation system including, but not limited to, implantable dual chamber and multi-chamber cardiac stimulation devices as well as external programming units for such stimulation devices. For example and without limitation, the present disclosure may be implemented in a multi-chamber cardiac stimulation device such as the stimulation device 10 depicted in FIG. 1.

Certain cardiac pacemakers and defibrillators incorporate a pacing lead in the right ventricle and may also include a second lead in the right atrium. High-burden right ventricle apical pacing may contribute to the development of pacing-induced cardiomyopathy and symptoms associated with heart failure (HF). Several pathophysiologic mechanisms have been implicated in the development of pacing-induced HF, each of which likely stems from non-physiological electrical and mechanical activation patterns produced by right ventricle pacing. His bundle pacing (HBP) has been shown to restore physiological activation patterns by utilizing a patient's intrinsic conduction system, even in the presence of bundle branch block. HBP has also been shown to provide significant QRS narrowing, with improved ejection fraction.

Another possible clinical application of HBP is cardiac resynchronization therapy (CRT). Conventional CRT systems include pacing from both a right ventricular and a left ventricular lead, and have been shown to be most effective for patients exhibiting a wide QRS complex and left bundle branch block. HBP has also been shown to be effective at narrowing the QRS complex in patients with left bundle branch block, likely due to restoration of conduction through the Purkinje fibers, which include right and left bundle fibers that are longitudinally dissociated. Therefore, what is thought of as left bundle branch block, can be a result of a proximal blockage within the His bundle that eventually branches to the left bundle. By pacing the His bundle distal to the blockage, a normalized QRS complex can be achieved in some patients. Theoretically, this pacing mode may provide even better results than known CRT treatments, as activation propagates rapidly through natural conduction pathways.

Depending on electrode position, pacing output, patient physiology, and other factors, pacing impulses delivered to the His bundle may result in capture of different cardiac tissue. As used herein, the term "capture" refers to depolarization of cardiac tissue in response to delivery of a pacing impulse. In the context of HBP, pacing of the His bundle will generally result in one of four capture scenarios: non-selective His bundle capture, selective His bundle capture, myocardium-only capture, or loss of capture (or non-capture). Non-selective capture refers to when a pacing impulse results in capture of both the His bundle and the local myocardium surrounding the His bundle. Because of the simultaneous depolarization of the His bundle and myocardium, non-selective His bundle capture generally results in a combined or condensed electrical response of the cardiac tissue as compared to normal heart activity in which the His bundle and myocardium are depolarized sequentially. Accordingly, non-selective His bundle capture may be characterized by a shortened delay between application of the pacing impulse and ventricular depolarization (e.g., on the order of 20 ms) because the myocardial depolarization propagates immediately without exclusively traveling through the His-Purkinje system. Nevertheless, because the His bundle is stimulated and captured, the QRS duration may be similar to the native QRS duration of the patient heart or slightly longer due to the myocardial excitation (e.g., 70-120 ms). In contrast to non-selective capture, selective His bundle capture refers to exclusive capture of the His bundle without depolarization of the surrounding myocardial tissue. With selective His bundle capture, the stimulus to ventricular depolarization interval is virtually the same as the native delay between His bundle activation and subsequent ventricular depolarization and the QRS duration is essentially identical to the native QRS duration. In myocardium-only capture, the tissue surrounding the His bundle is captured without capturing the His bundle, resulting in delayed signal conduction and activation. Finally, loss of capture generally refers to circumstances in which the applied stimulus is insufficient or otherwise unable to elicit a response from cardiac tissue. In such cases, backup pacing may be applied. For patients with branch bundle block or similar conduction disorders, the foregoing capture types may be further characterized by whether they result in correction of the conduction disorder. For example, a pacing impulse may result in any of non-selective His bundle capture with correction, non-selective His bundle capture without correction, selective His bundle capture with correction, selective His bundle capture without correction, myocardium only capture, or loss of capture.

While both selective and non-selective His bundle capture may be used to improve cardiac function, selective His bundle capture is generally preferred as the corresponding response more closely approximates natural heart function. However, due to the complexity and dynamic nature of certain cardiomyopathies and cardiac anatomies, selective His bundle capture may not be possible or, if possible at one time, may no longer be possible as a patient's condition changes over time. Moreover, a patient's condition may also progress such that His bundle capture (whether selective or non-selective) may become unavailable and, as a result, direct ventricular pacing may be required.

In light of the foregoing, this disclosure describes methods and apparatuses directed to improving HBP functionality of stimulation systems. In particular, this disclosure provides systems and methods for applying pacing impulses to the His bundle of a patient heart and classifying the resulting response. As described below, in certain implementations, classification of a response to His bundle pacing may be performed by analyzing particular characteristics of the response in the time domain that are indicative of specific capture types. Alternatively, classification of a response to His bundle pacing may include converting the response into a frequency spectrum and analyzing particular characteristics of the frequency spectrum.

The foregoing aspects of the present disclosure are discussed in further detail later in this disclosure; however, FIGS. 1-5 are now provided to generally describe the components and functionality of stimulation devices systems that may be used to implement aspects of the present disclosure. It should be appreciated that FIGS. 1-5 should be understood to be representative only and are therefore non-limiting. Rather, various aspects of the present disclosure may be implemented using any suitable stimulation system capable of pacing the His bundle and obtaining and analyzing corresponding response data. For example and unless otherwise specifically noted, stimulation systems in accordance with the present disclosure may include any number of leads configured to provide stimulation and/or pacing as described herein and may include either unipolar or bipolar leads. Moreover, it should further be understood that the methods disclosed herein may also be performed, at least in part, by an external testing or programming unit capable of receiving and transmitting data from an implantable stimulation device. Such data may include, without limitation, response data measured by the stimulation device and transmitted to the external unit and configuration data transmitted from the external unit to the stimulation device to configure the stimulation device.

With reference to FIG. 1, a stimulation device 10 is shown in electrical communication with a patient's heart 12 by way of four leads, 20, 21, 24, and 30 and is therefore suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage or atrial septum.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. In another embodiment, an additional electrode for providing left ventricular defibrillation shocking therapy may be included in the portion of the lead overlying the left ventricle, adjacent to the ring electrode 25.

The stimulation device 10 illustrated in FIG. 1 is generally configured as an implantable cardioverter-defibrillator (ICD) and generally includes functionality for pacing, sensing, and providing defibrillation to a patient heart. It should be appreciated however, that the ICD illustrated in FIG. 1 is just one example stimulation device that may implement aspects of the present disclosure. Other configurations and types of implantable stimulation devices incorporating aspects of the present disclosure are also contemplated. For example and without limitation, in at least one implementation, the stimulation device 10 of FIG. 1 may instead be configured as a pacemaker without defibrillation functionality and, in particular, a pacemaker configured to provide cardiac resynchronization therapy (CRT). In such implementations, some or all of the defibrillation coils illustrated on the various leads of FIG. 1 and their associated circuitry within the stimulation device 10 may be omitted. It should also be appreciated that the specific configuration of leads and placement of leads illustrated in FIG. 1 is intended merely as an example and other configurations are possible. For example, in one specific implementation, the coronary sinus lead 24 may instead be replaced with a left ventricle lead that extends and is implanted within the left ventricle for pacing and/or sensing of the left ventricle. More generally, implementations of the present disclosure are generally applicable to any suitable stimulation devices or systems currently known or later developed that provide His bundle pacing.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

The stimulation device 10 is further connected to a His bundle lead 21 having a His tip electrode 16, such as a helical active fixation device, and a His ring electrode 19 located proximal from the His tip electrode 16. In certain implementations, the His ring electrode 19 is located approximately 10 mm proximal the His tip electrode 16. The His bundle lead 21 may be transvenously inserted into the heart 12 so that the His tip electrode 16 is positioned in the tissue of the His bundle. Accordingly, the His bundle lead 21 is capable of receiving depolarization signals propagated in the His bundle and exiting the Purkinje fibers to the myocardium or delivering stimulation to the His bundle, creating a depolarization that can be propagated through the lower conductive pathways of the right and left ventricles (i.e., the right and left bundle branches and Purkinje fibers). An example of a His bundle lead suitable for delivering pacing impulses to the His bundle will be described in greater detail below in conjunction with FIG. 4.

Figure 2:
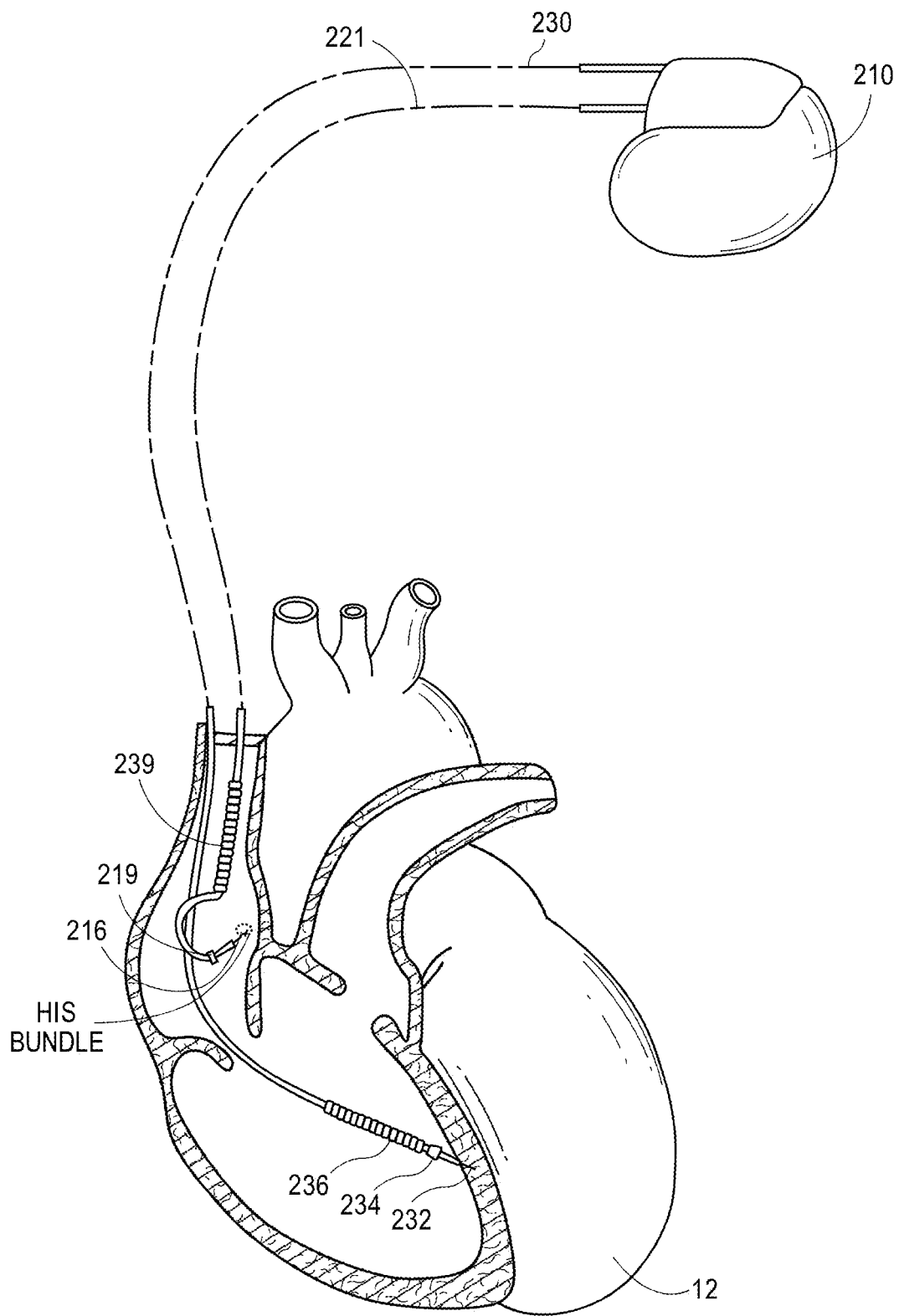
FIG. 2 is a simplified, partly cutaway view illustrating an alternative design of an implantable stimulation device, shown implanted into the right chambers of the patient's heart for delivering dual-chamber stimulation and shock therapy.

An alternative embodiment of the present disclosure is shown in FIG. 2 in which a dual chamber stimulation device 210 is in communication with one atrium, one ventricle, and the His bundle. Though not explicitly illustrated in FIG. 2, a right atrial lead 20 (shown in FIG. 1) can be optionally included. In such implementations, the stimulation device 210 maintains communication with the right atrium of the heart 12 via a right atrial lead 20 having at least an atrial tip electrode 22 and an atrial ring electrode 23 (which may be implanted in the patient's right atrial appendage as described earlier in connection with FIG. 1), and an SVC coil electrode 239

A His bundle lead 221, having a His tip electrode 216 and a His ring electrode 219, is positioned such that the His tip electrode 216 is proximate the His bundle tissue. The stimulation device 210 is shown in FIG. 2 in electrical communication with the patient's heart 12 by way of a right ventricular lead 230 including a right ventricular tip electrode 232, a right ventricular ring electrode 234, and a right ventricular coil electrode 236.

Figure 3:
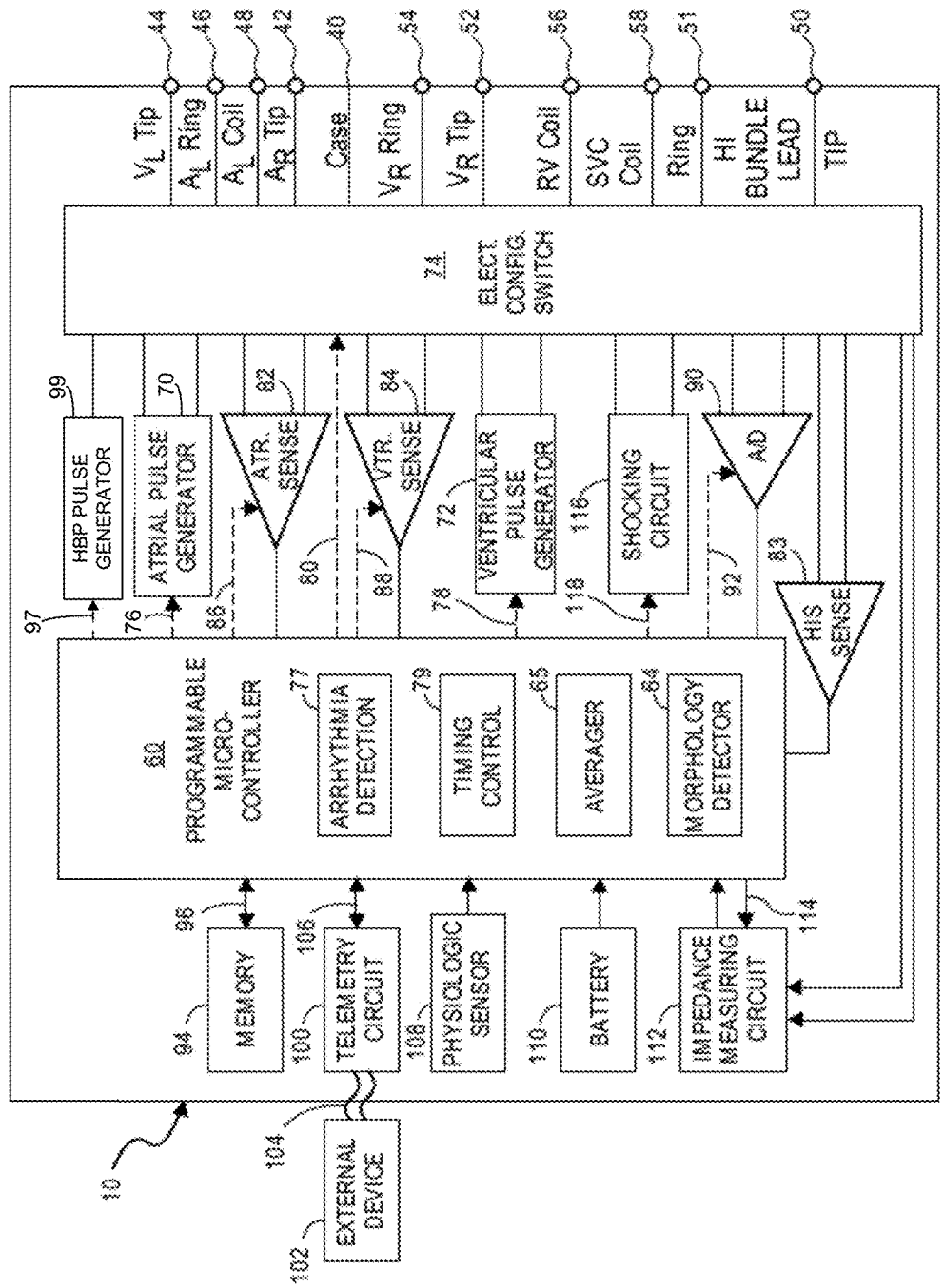
FIG. 3 is a functional block diagram of the multi-chamber implantable stimulation device of FIG. 1, illustrating the basic elements that provide pacing stimulation, cardioversion, and defibrillation in four chambers of the heart.

Referring now to FIG. 3, there is illustrated a simplified block diagram of the multi-chamber implantable stimulation device 10 of FIG. 2, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

Figure 4:
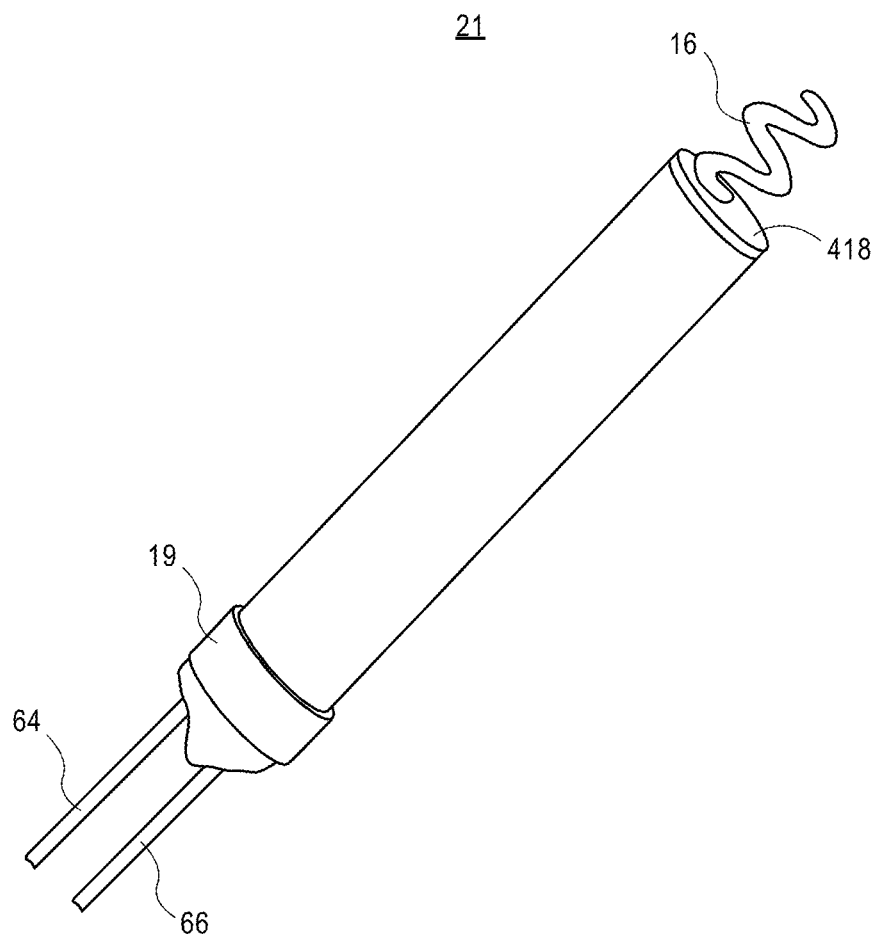
FIG. 4 is a partly fragmentary illustration of the distal end of the His bundle lead for use with the stimulation device of FIG. 3, depicting a tip electrode with an active fixation device and a non-traumatic conductive surface, and a ring electrode.

The housing 40 for the stimulation device 10, shown schematically in FIG. 4, is often referred to as the "can", "case" or "case electrode" and may be programmably selected to act as the return electrode for all "unipolar" modes. The housing 40 may further be used as a return electrode alone or in combination with one or more of the coil electrodes 28, 36, and 38 (shown in FIG. 1) for shocking purposes. The housing 40 further includes a connector (not shown) having a plurality of terminals 42, 44, 46, 48, 50-52, 54, 56, and 58 (shown schematically and, for convenience, next to the names of the electrodes to which they are connected). As such, to achieve right atrial sensing and pacing, the connector includes at least a right atrial tip terminal (AR TIP) 42 adapted for connection to the atrial tip electrode 22 (shown in FIG. 2).

To achieve left chamber sensing, pacing, and defibrillation (in applications in which the stimulation device 10 is an ICD), the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively (each shown in FIG. 1).

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the right ventricular coil electrode 36, and the SVC coil electrode 38, respectively (each shown in FIG. 1).

To achieve His bundle sensing, or sensing and stimulation, the connector further includes a His bundle lead tip terminal 50 and a His bundle lead ring terminal 51 which are adapted for connection to the His tip electrode 16 and the His ring electrode 19, respectively (each shown in FIG. 1).

At the core of the stimulation device 10 is a programmable microcontroller 60 which controls the various modes of stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present disclosure. Rather, any suitable microcontroller 60 may be used that carries out the functions described herein.

As shown in FIG. 3, an atrial pulse generator 70, a ventricular pulse generator 72, and a His bundle pacing (HBP) pulse generator 99 generate pacing stimulation pulses for delivery by the right atrial lead 20, the right ventricular lead 30, the coronary sinus lead 24, and/or the His bundle lead 21 via an electrode configuration switch 74. As previously noted, in certain applications, the coronary sinus lead 24 may instead be substituted with a left ventricle lead. It is understood that in order to provide stimulation therapy in each of the chambers of the heart and/or to specific structures of the heart (e.g., the His bundle), the atrial, ventricular, and HBP pulse generators 70, 72, 99 may include dedicated, independent pulse generators, multiplexed pulse generators, or shared pulse generators. The pulse generators 70, 72, 99 are controlled by the microcontroller 60 via appropriate control signals 76, 78, 97 to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g., pacing rate) as well as to keep track of the timing of refractory periods, blanking intervals, noise detection windows, evoked response windows, alert intervals, marker channel timing, etc., which is well known in the art.

According to one embodiment of the present disclosure, timing control circuitry 79 also controls the onset and duration of a His signal sensing window during which a depolarization signal conducted through the AV node to the His bundle can be detected. Timing control circuitry 79 also controls a timing delay provided after a detected His signal detection, prior to the delivery of a right and/or left ventricular stimulation pulse.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24 (or left ventricle lead), and the right ventricular lead 30, through the switch 74 for detecting the presence of cardiac activity in each of the four chambers of the heart. Accordingly, the atrial (ATR. SENSE) and ventricular (VTR. SENSE) sensing circuits 82, 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

According to one implementation of the present disclosure, a His sensing circuit 83 is selectively coupled to the His bundle lead 21 (shown in FIG. 1) for detecting the presence of a conducted depolarization arising in the atria and conducted through the His bundle via the AV node. As used herein, each of the atrial sensing circuit 82, the ventricular sensing circuit 84, and the His sensing circuit 83, includes a discriminator, which is a circuit that senses and can indicate or discriminate the origin of a cardiac signal in each of the cardiac chambers.

As illustrated in FIG. 3, the His sensing circuit 83 is shown as a dedicated circuit within the stimulation device 10. However, it should be appreciated that in certain implementations, His-related functionality may instead be provided by repurposing other pacing and sensing channels and circuitry of the stimulation device 10. For example, the stimulation device 10 may be reprogrammed such that a pacing channel, a sensing channel, and associated circuitry initially programmed for use in sensing and pacing one of the atria or ventricles may instead be reconfigured to pace and sense the His bundle.

Each sensing circuit 82-84 preferably employs one or more low power, precision amplifiers with programmable gain and/or automatic gain control, bandpass filtering, and a threshold detection circuit to selectively sense the cardiac signal of interest. The automatic gain control enables the device 10 to deal effectively with the difficult problem of sensing the low amplitude signal characteristics of atrial or ventricular fibrillation.

The outputs of the sensing circuits 82-84 are connected to the microcontroller 60 which, in turn, is able to trigger or inhibit the atrial and ventricular pulse generators 70, 72, respectively, in a demand fashion in response to the absence or presence of cardiac activity in the appropriate chambers of the heart.

The atrial and ventricular sensing circuits 82, 84, in turn, receive control signals over signal lines 86, 88, from the microcontroller 60 for purposes of controlling the gain, threshold, polarization charge removal circuitry (not shown), and the timing of any blocking circuitry (not shown) coupled to the inputs of the sensing circuits 82, 84.

Similarly, the output of the His sensing circuit 83 is connected to the microcontroller 60 which, in turn, is able to trigger or inhibit the HBP pulse generator 99 in a demand fashion in response to the absence or presence of cardiac activity associated with the His bundle. The His sensing circuit 83 may also receive control signals from the microcontroller 60 for purposes of controlling gain, threshold, polarization charge removal circuitry, and the timing of any blocking circuitry coupled to the inputs of the His sensing circuit 83.

Control and/or configuration of the HBP pulse generator 99 may be based on measurements related to activity of other structures/chambers of the heart instead of or in addition to the His bundle. So, for example and without limitation, the HBP pulse generator 99 may also be triggered, inhibited, calibrated, or configured based on outputs from the atrial and ventricular sensing circuits 82-84 or any other similar sensing circuit adapted to measure electrical activity of the heart.

For arrhythmia detection, the stimulation device 10 includes an arrhythmia detector 77 that utilizes the atrial and ventricular sensing circuits 82, 84, to sense cardiac signals to determine whether a rhythm is physiologic or pathologic. As used herein "sensing" is reserved for the noting of an electrical signal, and "detection" is the processing of these sensed signals, which may include noting the presence of an arrhythmia or other cardiac event. The timing intervals between sensed events (e.g., P-waves, R-waves, and depolarization signals associated with fibrillation) may then be classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"), if any. In certain implementations, the stimulation device 10 may also include a morphology detector 63 that can, e.g., assess characteristics such as amplitude, area under curves, polarity, and shape, of detected cardiac rhythms.

Cardiac signals may be applied to the inputs of an analog-to-digital (A/D) data acquisition system 90, which is represented by an A/D converter 90. The data acquisition system 90 is configured to acquire intracardiac electrogram signals, convert the raw analog data into a digital signal, and store the digital signal for later processing and/or telemetric transmission to an external device 102. The data acquisition system 90 may be coupled to any of the right atrial lead 20, the His bundle lead 21, the coronary sinus lead 24, or the right ventricular lead 30 through the switch 74 to sample cardiac signals across any pair of desired electrodes.

In one embodiment, the data acquisition system 90 is coupled to the microcontroller 60, or to other detection circuitry, for detecting a desired feature of the His bundle signal. In one embodiment, an averager 65 may be used to determine a sliding average of the His bundle signal during a His signal sensing window using known or available signal averaging techniques.

Advantageously, the data acquisition system 90 may be coupled to the microcontroller 60, or other detection circuitry, for detecting an evoked response from the heart 12 in response to an applied stimulus, thereby aiding in the detection of capture. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred. As described below in further detail, one or both of the microcontroller 60 and the external device 102 may also be configured to classify a capture event (e.g., as selective capture, non-selective capture, myocardium-only capture, or loss of capture).

Capture detection may occur on a beat-by-beat basis or on a sampled basis. Preferably, a capture threshold search is performed at least once a day (or similar interval) during at least the acute phase (e.g., the first 30 days following device implant) and less frequently thereafter. In one non-limiting example, a capture threshold search may begin at a desired starting point (either a high energy level or the level at which capture is currently occurring) and decrease the energy level until capture is lost. The minimum energy at which capture is consistently obtained is known as the capture threshold. Thereafter, a safety margin can be automatically or programmably added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In certain implementations, the stimulation device 10 may further include a physiologic sensor 108, commonly referred to as a "rate-responsive" sensor to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, stimulation delays, etc.) at which the atrial and ventricular pulse generators 70, 72 generate stimulation pulses.

A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate, and/or minute ventilation, pH of blood, ventricular gradient, etc. However, any suitable sensor may be used which is capable of sensing a physiological parameter which corresponds to the exercise state of the patient. The type of sensor used is not critical to the present disclosure and is shown only for completeness.

The stimulation device 10 additionally includes a battery 110 which provides operating power to all of the circuits shown in FIG. 4. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 is shown in FIG. 3 as having an impedance measuring circuit 112 which is enabled by the microcontroller 60 via a control signal 114. The known uses for an impedance measuring circuit 112 include, but are not limited to, lead impedance surveillance during the acute and chronic phases for detecting proper lead positioning or dislodgement; detecting operable electrodes and conductors; and automatically switching to an operable pair if dislodgement or electrical disruption occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

In certain implementations of the present disclosure, the device 10 may be configured to perform beat-by-beat impedance monitoring in conjunction with measuring and monitoring other electrical activity (e.g., generating electrograms (EGMs)) for each beat. In such applications, the measured impedance may generally provide further information regarding the occurrence and potential cause of changes in the electrical activity, including, without limitation, changes in His bundle capture type or capture quality.

According to one implementation of the present disclosure, the His tip electrode 16 and His ring electrode 19 may be selectively coupled via switch 74 to the impedance measuring circuit 112 for performing a tissue impedance measurement. The tissue impedance measurement may be made to determine the location of the His bundle as the His tip electrode 16 or mapping collar 418 as shown in FIG. 4 is advanced along the endocardial surface of the right atrium. In other implementations of the present disclosure, alternative approaches for mapping the intrinsic conduction signals of the His bundle and associated tissue may be used. For example and without limitation, in at least one implementation an electrophysiology (EP) catheter may be used to identify a location for the His tip electrode 16.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (for example, up to 0.5 joules), moderate (for example, 0.5-10 joules), or high energy (for example, 11-40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and the SVC coil electrode 38. As noted above, the housing 40 may act as an active electrode in combination with the right ventricular electrode 36, or as part of a split electrical vector using the SVC coil electrode 38 or the left atrial coil electrode 28 (i.e., using the right ventricular electrode 36 as a common electrode). As previously noted, the implementation illustrated in FIG. 1 is provided as an example and other configurations are possible. For example, in other implementations, the high voltage coils for both RV coil and SVC coil may be disposed on the right ventricle lead as opposed to the RA lead.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

A more detailed illustration of the His bundle lead 21 is shown in FIG. 4. At the distal end of the lead 21 is the His bundle tip electrode 16. The His bundle tip electrode 16 is, or includes, an active fixation device, such as a helical, "screw-in," device that allows stable fixation of the electrode in the His bundle tissue.

The distal end of the His bundle lead 21 is further provided with a non-traumatic conductive surface (also referred to herein interchangeably as a mapping collar) 418. The non-traumatic conductive surface 418 is advantageously used to make electrical measurements that indicate the location of the His bundle without having to anchor the His bundle tip electrode 16 into the endocardial tissue. The non-traumatic conductive surface 418 and the His bundle tip electrode 16 are electrically coupled within the lead body of the His bundle lead 21 and together form one conductive element for the purposes of sensing, stimulation, and impedance measurements.

The His bundle lead 21 is also provided with a His ring electrode 19. The His ring electrode 19 is preferably spaced between approximately 2 mm and 30 mm, but preferably 10 mm, from the His tip electrode 16. The His ring electrode 19 may function as the return electrode during bipolar sensing, stimulation or impedance measurement operations.

The His tip electrode 16 and the His ring electrode 19 are each connected to flexible conductors 64, 66, respectively, which may run the entire length of the His bundle lead 21. The flexible conductor 64 is connected to the His tip electrode 16 and is electrically insulated from the flexible conductor 66 by a layer of insulation. The conductor 66 is connected to the His ring electrode 19. The flexible conductors 64, 66 serve to electrically couple the His ring electrode 19 and the His tip electrode 16 to the His ring electrode terminal 51 and the His tip electrode terminal 50, respectively. One example of the His bundle lead 21 is available from St. Jude Medical CRMD as lead model No. 2088T.

Figure 5:
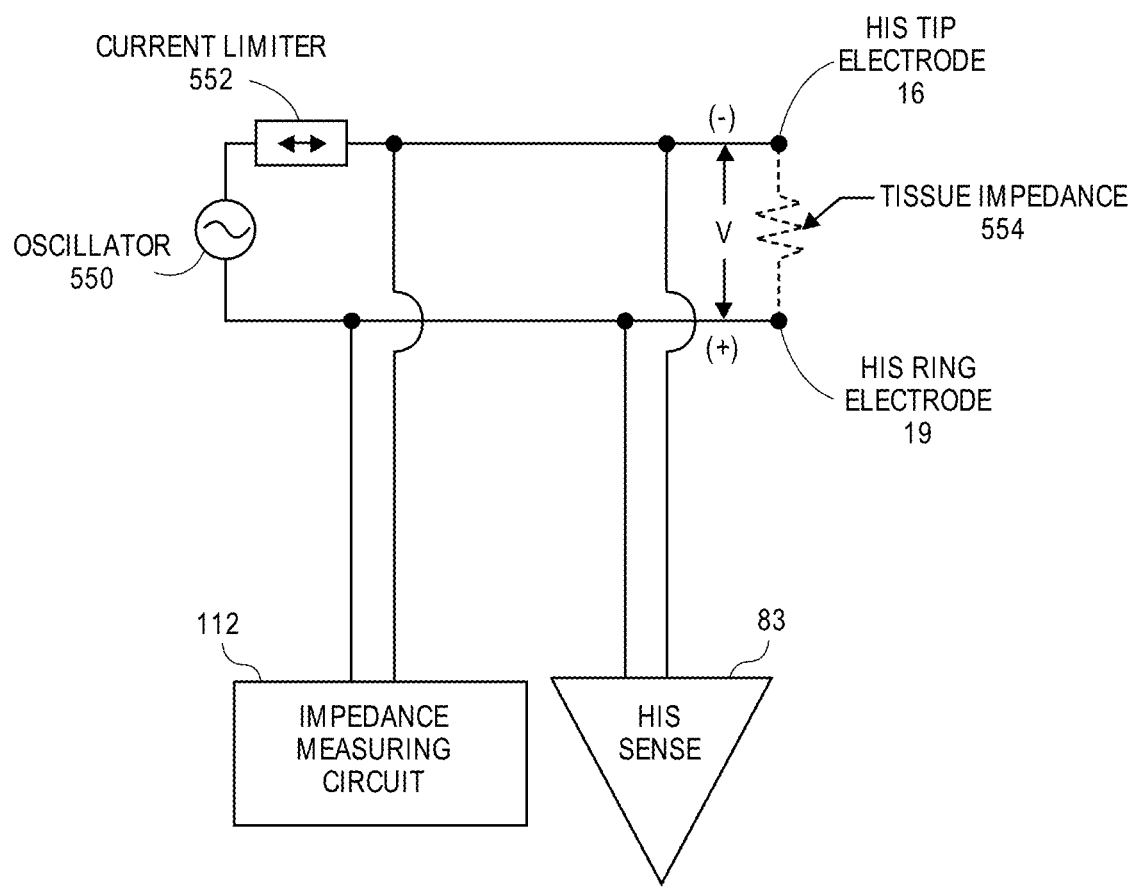
FIG. 5 is an equivalent circuit diagram illustrating a tissue impedance measurement method using the lead of FIG. 4 and the stimulation device of FIG. 3 for locating the His Bundle.

The equivalent circuit diagram depicted in FIG. 5 represents a model by which His signals and a tissue impedance measurement can be made using the His bundle lead 21 of FIG. 4. An excitation current is applied through the His tip electrode 16. A voltage signal can then be measured between the His tip electrode 16 (or the non-traumatic conductive surface 418) and the His ring electrode 19 in a bipolar fashion. The voltage signal is related to the supplied current and the tissue impedance 554 associated with the tissue in contact with the His tip electrode 16. Thus, the measured voltage signal is processed by the impedance measuring circuit 112 to determine the impedance of the tissue in contact with His tip electrode 16. The impedance equals the voltage divided by the current.

The His tip electrode 16 may then be secured in the His bundle thereby anchoring the His tip electrode 16 in contact with the His bundle tissue. The electrogram signal arising from the His bundle can then be received by the His sensing circuit 83. A bypass filter (not shown) that allows signals ranging from 30-200 Hz to be received may be used to block the high frequency alternating current excitation signal produced by the oscillator 550.

It should be appreciated that the His bundle leads and associated components illustrated in FIG. 4 are provided merely as examples and should not be viewed as limiting this disclosure to requiring any particular type of lead. Rather, aspects of the present current disclosure may be implemented using any suitable His bundle lead capable of being implanted at or near the His bundle and providing pacing impulses to the His bundle.

Beat-to-Beat his Bundle Pacing Using Time Domain Analysis

As previously noted, pacing of the His bundle may result in different responses identified by the particular tissue activated by the pacing impulse. For example, selective capture refers to when pacing of the His bundle results in capture of the His bundle only and propagation of the pacing impulse occurs using the heart's natural pathways. In contrast, non-selective capture refers to capture of both the His bundle and local myocardium. Finally, myocardium-only capture occurs when pacing of the His bundle captures only the myocardium surrounding the His bundle but not the His bundle itself. Such capture generally results in the impulse propagating down the septum and to the ventricles at a relatively slow velocity as compared to the other types of capture which involve activation of faster, intrinsic conduction paths of the heart associated with the His-Purkinje system. It should also be appreciated that a pacing impulse may fail to capture either of the His bundle or the surrounding myocardium, resulting in what is generally referred to herein as non-capture or loss-of-capture. In such cases, the intrinsic beat of the heart may be measured or otherwise come through.

In light of the foregoing, measuring and analyzing the response of the heart to pacing of the His bundle can enable identification of the particular type of capture (or non-capture) resulting from the applied pacing impulses. In response to identifying certain responses, the stimulation device may also be configured to recalibrate (e.g., by conducting a capture threshold search) or otherwise adjust one or more operational parameters. For example, an intracardiac electrogram (IEGM) may be captured in conjunction with application of a pacing impulse to the His bundle. Characteristics of the IEGM may then be measured to determine the type of capture (if any) resulting from the pacing impulse. In certain implementations of the present disclosure, such analysis may be conducted in the time-domain, e.g., by identifying and measuring characteristics of the response as indicated in the IEGM over time.

As described below in further detail, analysis of the time-domain characteristics of the heart's response to a pacing impulse (e.g., as recorded as an IEGM) can be used to automatically determine what type of capture, if any, has occurred in response to the pacing impulse. Such analysis may be based on characteristics of the total response (e.g., the overall shape and duration of the complete IEGM waveform resulting from the impulse), select portions of the response (e.g., time intervals between certain identifiable events in the response), or combinations thereof. In certain implementations, classifying the response as a particular capture type may require analysis of multiple characteristics. For example, a first characteristic may be analyzed to distinguish between selective capture and one of non-selective or myocardium-only capture and a second characteristic may be analyzed to further distinguish between non-selective and myocardium-only capture after selective capture has been effectively eliminated from consideration.

Although various measurements of the response to a pacing impulse may be used to determine capture and capture type, Table 1 below provides a summary of various measurements and qualitative characteristics of such measurements as they pertain to the different capture classifications. Certain of the measurements listed in Table 1 are explored further below.

TABLE 1

Qualitative Comparison of Capture Types

| | Capture Type | | | |
|---|---|---|---|---|
| Measurement | Selective | Non-Selective | Myocardium-Only | Non-Capture |
| Morphology | Similar to natural sinus rhythm | Wider than natural sinus rhythm | Narrower than natural sinus rhythm | Long delay between impulse and onset of QRS complex, if any No change when AV delay shortened high R-to-R variability |
| Stimulation to unipolar peak | Similar across all capture types | | | |
| Simulation to Bipolar Peak | Long | Short | Short | Longer than selective capture |
| Stim to unipolar max(−dV/dt) | Long | Short | Short | long |
| IEGM QRS width | Narrow | Wide | Wide | Narrow |
| Unipolar Peak to Peak width (−ve to +ve peak) | Short | Short | Long | Short |
| Stimulation to last peak | Short | Short | Long | Long |
| Stimulation to end of dV/dt peak | Short | Short | Long | Long |
| Unipolar amplitude | Small | Large | Large | Small |
| Unipolar downstroke/upstroke slope | Steep | Steep | Less steep | Steep |
| IEGM QRS integral | Small | Intermediate | Large | Small |

Morphology generally refers to the overall size and shape of the IEGM waveform. As previously discussed in this disclosure, analyzing morphology of an IEGM waveform may include comparing the IEGM waveform to one or more templates representative of different capture types. For example, templates for each of selective, non-selective, and myocardium only capture may be stored within the stimulation device. Each template may in turn include a series of points, such as ordered pairs of time and signal amplitude, defining a model waveform corresponding to the particular type of capture.

In conjunction with pacing of the His bundle, the stimulation device may collect and store responsive EGM data and compare such data to the templates. Similar to the template, the response data may be collected and stored as a series of points, such as ordered pairs of time and signal amplitude. The stimulation device may then correlate the template to the response data based on a pacing time (or other point common to each of the template and response data) and compare the subsequent points by cross-correlation. Based on such a comparison a score or similar metric, such as a cross-correlation coefficient, describing the "fit" of the response to the template may be calculated. If the comparison metric exceeds a threshold (e.g., an 80% match, a cross-correlation coefficient of 0.8, etc.), the template and response may be considered a match and the response may be classified accordingly as resulting in the capture corresponding to the template. If the score falls below the threshold, additional comparisons of the response to other templates may be performed or the response may be classified as non-capture/loss-of-capture or undefined. Alternatively, the specific way in which the response deviates from the template may be used to identify the type of capture or non-capture.

IEGM or similar templates for the different types of capture may be dynamically generated and stored during an in-office visit following implantation of the stimulation device (e.g., a post-operative visit or other follow up office visit). Alternatively or in addition to such initial setup, the templates may be generated during an automatic configuration and calibration routine executed by the stimulation device. In either case, prior to generation of the IEGM templates, an initial threshold search/test may be conducted to determine impulse parameters for each type of capture. A non-limiting example of such an initial threshold search/test including generating and storage of morphology templates is provided in U.S. patent application Ser. No. 15/653,357, which is incorporated herein by reference in its entirety. Impulses may then be applied according to the results of the threshold test and the corresponding response may be recorded and stored as a template. A template may correspond to a single response or may be an average or other mathematical combination of multiple responses. In addition to templates for each type of capture, a template corresponding to the heart's intrinsic response/natural sinus rhythm may also be generated and stored.

Comparison of a measured response to the stored templates may facilitate identifying what, if any, capture has occurred. For example, as noted in Table 1, while a response resulting from selective capture will generally appear similar to an intrinsic response/sinus rhythm, deviation from sinus rhythm may be indicative of either non-selective or myocardium-only capture. For example, such deviation may appear as a relative widening of the response waveform as compared to that of sinus rhythm or selective capture.

Other metrics that may be used to identify and classify what type of capture has occurred may be based on the timing between stimulation and particular characteristics of the resulting response. In certain specific implementations and without limitation, the time interval between application of a pacing impulse and any of a bipolar peak, a unipolar maximum rate of voltage change (dV/dt), or a last peak of the QRS complex may be measured and used to identify and classify capture type. Each of these metrics provides an indication of how rapidly the QRS complex arises following application of a pacing impulse and indirectly indicates activation time of the ventricles and QRS width. To the extent the interval is relatively short, non-selective or myocardium-only capture is likely. More specifically, during selective capture, a longer delay (as compared to non-selective or myocardium-only capture) is observable between pacing of the His bundle and initiation of the QRS complex due to the impulse having to propagate through the heart's intrinsic electrical pathways. In contrast, in each of non-selective and myocardium-only capture the pacing impulse at least partially bypasses such intrinsic pathways and local propagation occurs around the stimulus, resulting in the QRS complex arising sooner than in the case of selective capture.

In light of the foregoing, measuring the delay between application of a pacing impulse and the occurrence of portions of the QRS complex having particular characteristics may be used to determine a type of capture. For example, values, ranges of values, or templates for some or all of the different capture scenarios may be stored in memory of the stimulation device. Following application of a pacing impulse, a measured response (e.g., an IEGM) to the impulse may be analyzed relative to the stored information. Such analysis may generally include identifying each of the application of the pacing impulse, the relevant characteristics of the QRS complex of the response, and the delay therebetween and then comparing the delay to the stored delay information. Based on the comparison, the stimulation device may determine what, if any, type of capture has occurred.

In still other implementations of the present disclosure, characteristics of the QRS complex independent of the timing from the pacing impulse may be used to determine what type of capture has occurred. For example, conduction velocity through the heart generally indicates capture type with each of selective and non-selective capture resulting in faster conduction than myocardium-only capture. In light of this observation, one example metric indicative of conduction velocity is the peak-to-peak interval of the QRS complex and, in particular, the negative-to-positive peak-to-peak interval between the Q and R points of the QRS complex. More generally, however, the interval between any two portions of the QRS complex may be used to determine capture type.

As another example, the total QRS duration may also be used to determine capture type. More generally, each of selective and non-selective capture results in a wider QRS complex than myocardium-only capture or selective capture. Determining total QRS duration may include first calculating a derivative of the QRS complex, which may facilitate identification of the start and end of the QRS complex. As yet another example metric, the integral the QRS complex (or a rectified version thereof) may also be used to determine capture type. Non-limiting examples of each of the foregoing approaches are discussed in U.S. patent application Ser. No. 15/655,357, which was previously incorporated herein by reference.

The foregoing examples should be regarded as a non-limiting list of response characteristics that may be used to distinguish between capture types and, as a result, other distinguishing characteristics of the response data may be considered.

As previously mentioned, Table 1 provides qualitative differences between various measurements as they relate to each capture type. Although specific values for the foregoing example metrics may vary from patient-to-patient, Table 2, below, provides a summary of quantitative values obtained experimentally for at least some of the measurements.

TABLE 2

Experimental Results for Metrics Indicating Capture Type (mean ± standard deviation from 25 patients)

| | Capture Type | | | |
|---|---|---|---|---|
| Measurement | Selective | Non-Selective | Myocardium-Only | Intrinsic |
| Stimulation to unipolar peak (ms) | 88 | 88 | 86 | N/A |
| Stimulation to bipolar peak (ms) | 120 ± 17 | 59 ± 17 | 53 ± 11 | 182 ± 95 |
| Stimulation to unipolar max dV/dt (ms) | 75 | 29 | 45 | N/A |
| Peak to peak interval (ms) | 25 | 39 | 90 | 41 |
| Stimulation to last peak (ms) | 121 | 137 | 176 | N/A |
| Stimulation to end of dV/dt peak | 125 | 140 | 180 | N/A |
| Unipolar width (Tip-Can) | 67 ± 24 | 91 ± 15 | 102 ± 10 | 71 ± 26 |
| Unipolar width (Ring-Can) | 66 ± 15 | 98 ± 25 | 104 ± 12 | 65 ± 26 |
| Integral of Rectified QRS | 27 | 242 | N/A | 29.7 |

The values included in Table 2 should be considered as examples only and are provided primarily as examples of the variation between capture types for the metrics listed. As previously noted, specific values for each capture type may vary between patients. So, for example, the time delay between application of a stimulation impulse and the bipolar peak may generally indicate selective capture when it exceeds about 70 ms or loss of capture when it exceeds 140 ms. Similarly, the peak-to-peak interval, the time delay between application of the impulse and a last peak of the response, and the time delay between application of the impulse and the end of the peak slope of the response may generally indicate myocardium-only capture when they exceed about 60 ms, about 150 ms, and about 150 ms, respectively. Moreover, while specific values of measurements are included in Table 2, it should be appreciated that, in most cases, inherent variability in the structure and function of the heart may result in variability from beat-to-beat for the listed metrics even for the same patient. Accordingly, while indicated as individual values, in at least certain implementations of the present disclosure, the values may instead correspond to an average or similar statistical measure corresponding to multiple beats. The values provided in Table 2 are also examples from a relatively small set of patient and the specific values for the characteristics in Table 2 can vary from patient to patient. As a result, in at least some implementations of the present disclosure, one or more metrics used to determine capture type may be specifically measured or derived for a given patient instead of using predetermined values collected from multiple patients.

Based on the foregoing examples of response characteristics and their corresponding use in determining capture type, stimulation systems in accordance with the present disclosure may apply pacing impulses, analyze the resulting responses to determine capture type, and, if an undesirable or suboptimal response is detected, modify operational characteristics of the stimulation device accordingly.

Figure 6:
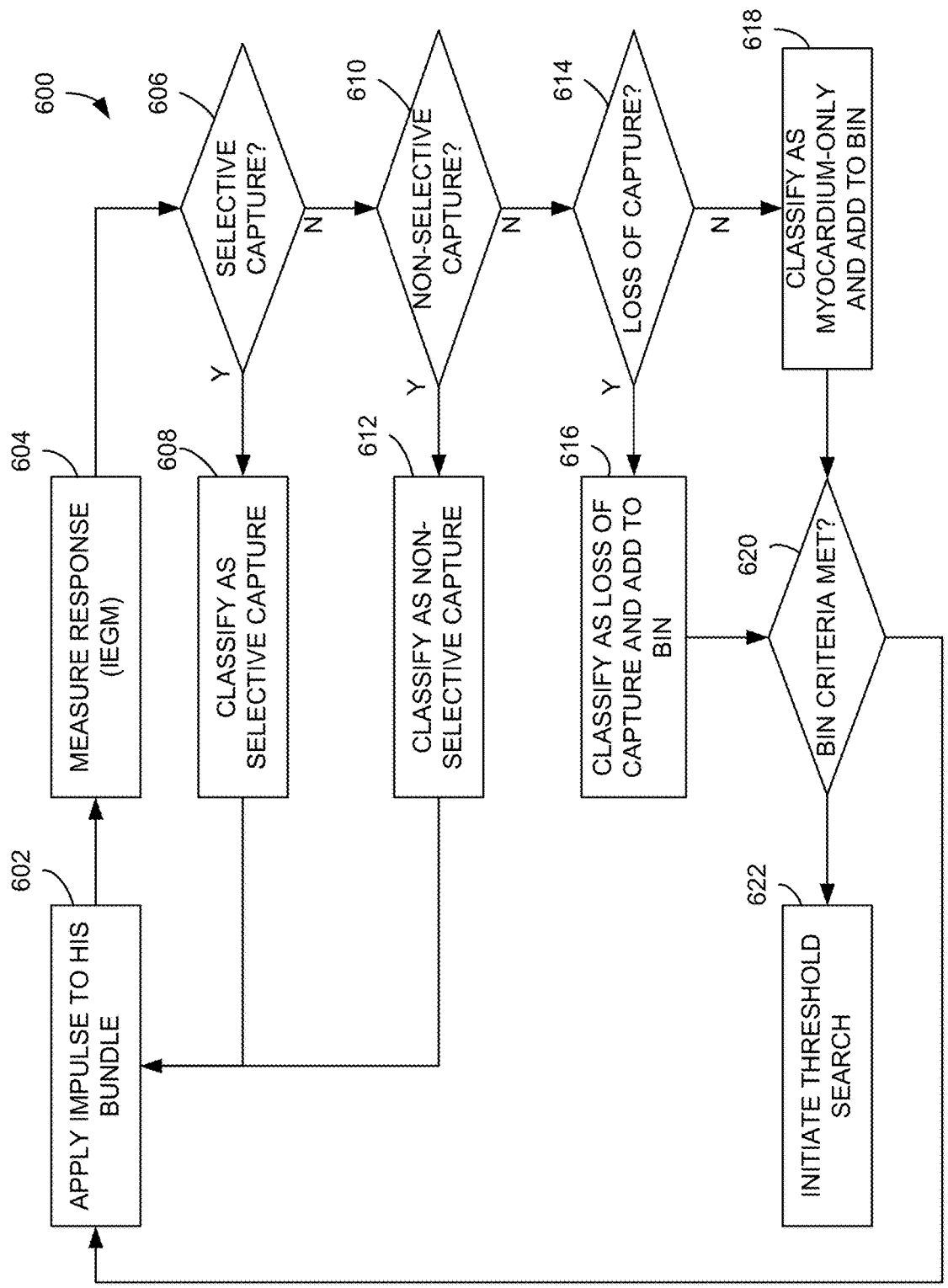
FIG. 6 is a flow chart illustrating a method for identifying capture types based on time-domain characteristics of a response to a pacing impulse.

FIG. 6 is a flow chart illustrating a method 600 for performing His bundle pacing and may be executable by a stimulation device in accordance with the present disclosure. In general and as described below in further detail, the method 600 includes applying a pacing impulse to the His bundle, measuring the corresponding response of the heart, and evaluating the response to determine what, if any, capture has occurred. Due to similarities in responses between different capture types, the method 600 specifically includes an elimination approach in which the measured response is first evaluated to determine whether it corresponds to selective capture. More specifically, the response is first analyzed to determine if it has characteristics indicative of selective capture only. If not, subsequent analysis is performed to determine whether the response corresponds to myocardium only or non-selective capture. As a result, the process of distinguishing between myocardium only and non-selective capture can rely on metrics for which values may overlap for selective capture. In the event of myocardium only or non-capture, the method also includes taking various remedial steps, including initiating a threshold search.

At operation 602, a stimulation/pacing impulse is applied to the His bundle and, at operation 604, the corresponding response of the heart is measured, such as by using an intracardiac electrogram (IEGM). Although operation 604 is indicated in FIG. 6 as occurring after operation 602, it should be appreciated that the stimulation device may monitor/measure electrical activity of the heart constantly or may begin recording data prior to application of the stimulation/pacing impulse applied at operation 602. By doing so, the application of the impulse may also be measured and identified and, as a result, used in determining the type of capture resulting from the application of the impulse at operation 604.

The stimulation device may first analyze the response obtained in operation 604 to determine whether the pacing impulse resulted in selective capture (operation 606). Such a determination may be conducted in various ways, however, as indicated in Table 1, selective capture may generally result in a response that is distinguishable from each of non-selective and myocardium-only capture with respect to one or more of: (1) overall morphology; (2) time between stimulation and bipolar peak; (3) time between stimulation and unipolar maximum slope; (4) QRS width; (5) unipolar amplitude; and (6) QRS integral. Accordingly operation 606 may generally include identifying one of the foregoing characteristics and comparing the characteristic to a corresponding stored value, range of values, or template for selective capture. If selective capture is detected, the stimulation device classifies the response as selective capture (operation 608) and may proceed to generate an impulse for and analyze the next heartbeat (operations 602, 604).

If, on the other hand, the stimulation device determines that selective capture has not occurred, the stimulation device may further analyze the response obtained in operation 604 to determine whether the pacing impulse resulted in non-selective capture (operation 610). Similar to the previous analysis for determining selective capture, non-selective capture may be determined in various ways. However, as indicated in Table 1, similar to selective capture, non-selective capture may be distinguished by one or more of: (1) overall morphology; (2) time between stimulation and bipolar peak; (3) time between stimulation and unipolar maximum slope; (4) QRS width; (5) unipolar amplitude; and (6) QRS integral. Accordingly operation 610 may generally include identifying one of the foregoing characteristics and comparing the characteristic to a corresponding stored value, range of values, or template for non-selective capture.

If non-selective capture is detected, the stimulation device classifies the response as non-selective capture (operation 612) and may proceed to generate an impulse for and analyze the next heartbeat (operations 602, 604).

If neither selective nor non-selective capture is detected, the stimulation device may determine whether loss of capture has occurred (operation 614). Again, such a determination may be conducted in various ways, however, as indicated in Table 1, loss of capture may generally result in a response that is distinguishable from other capture types with respect to one or more of: (1) overall morphology; (2) time between stimulation and bipolar peak; (3) time between stimulation and unipolar maximum slope; (4) QRS width; (5) unipolar amplitude; and (6) QRS integral. Accordingly operation 614 may generally include identifying one of the foregoing characteristics and comparing the characteristic to a corresponding stored value, range of values, or template for loss of capture/non-capture.

If the response is identified as being indicative of loss of capture in operation 614, the stimulation device may classify the response as loss of capture and may generate a "bin" entry, log entry, or similar record for purposes of tracking loss of capture events (operation 616). If, on the other hand, the response is not indicative of loss of capture, the response may be classified as myocardium-only capture and a corresponding bin entry may be generated (operation 618).

It should be appreciated that instead of testing for loss of capture at operation 614, the stimulation device may instead test for myocardium-only capture first. To do so, the stimulation device may further analyze one or more of: (1) the peak-to-peak time interval (PPI); (2) the stimulation to last peak time interval; and (3) the stimulation to an end of the dV/dt peak. With respect to the peak-to-peak time interval, for example, myocardium only capture generally results in significantly greater peak-to-peak time intervals (e.g., ~90 ms versus ~40 ms or less), stimulation to last peak time intervals (e.g., ~175 ms versus ~140 ms or less), and stimulation to end of dV/dt peak intervals as compared to non-selective (or selective) capture.

As previously noted, whether the response is identified as being indicative of loss of capture or myocardium-only capture, the stimulation device may generate a corresponding log or "bin" entry. In certain implementations, such an entry may simply indicate that loss of capture or myocardium-only capture occurred and provide a tally of the number of loss of capture or myocardium-only capture events. In other implementations, each entry may further contain information regarding the pacing impulse (e.g., energy and duration) that may be subsequently used to perform a threshold search.

As indicated in the method 600, such a threshold search may be initiated in response to the log/bin meeting certain criteria (operation 620). Such criteria may include, among other things, the number of log/bin entries (i.e., a certain number of myocardium-only captures or loss of capture events) being generated, a certain number of consecutive beats for which myocardium-only capture or loss of capture has occurred (e.g., five consecutive beats), a certain proportion of beats being myocardium-only capture or loss of capture (e.g., five out of the last ten beats), or any other similar criteria. If such criteria are met, the stimulation device may initiate a threshold search (operation 622) to recalibrate the stimulation device and, in particular, the pacing impulse parameters to increase the likelihood of non-selective or selective capture. If the criteria is not met, the stimulation device may simply move on to providing an impulse for and analyzing the next heartbeat (i.e., operations 602, 604). Notably, in certain implementations separate bins/logs for myocardium-only capture and loss of capture may be maintained and separate criteria may be applied to each such bin to determine when to initiate a threshold search.

It should also be appreciated, however, that the specific order of tests for capture type implemented by the stimulation device may vary. More specifically, the stimulation device may test the response data for any of selective capture, non-selective capture, myocardium-only capture, or loss of capture in any order. In one implementation, loss of capture may be identified in conjunction with determining whether selective or non-selective capture has occurred. For example, subsequent to determining the response includes characteristics of selective capture (e.g., a positive result in operation 606), the stimulation device may determine whether the response is actually indicative of a loss of capture due to shared response characteristic ranges or values for selective capture and loss of capture. Although various characteristics of the response may be analyzed to do so, in at least one specific instance the stimulation device may analyze a time between application of the impulse and the resulting bipolar peak as such time is generally shorter in the loss of capture case than in the selective capture case. Similar analysis may be conducted in combination with the other capture types by analyzing response characteristics that differ between the particular capture case (e.g., non-selective or myocardium only capture) and loss of capture/non-capture. Non-limiting examples of such characteristics are provided above in Table 1.

In certain implementations, if the stimulation device identifies the response as indicating loss of capture, a loss of capture routine or process may be initiated. The loss of capture routine may generally include one or more steps directed to addressing a loss of capture event and may include, among other things, delivery of a backup impulse, generation of a bin of log entry for tracking loss of capture events, evaluation of a log or bin to determine whether a capture threshold test (or similar recalibration) is required, and initiating a capture threshold test (or similar recalibration). Although the specific details of the loss of capture routine may vary, one example loss of capture routine is discussed in further detail below in the context of FIG. 7.

Figure 7:
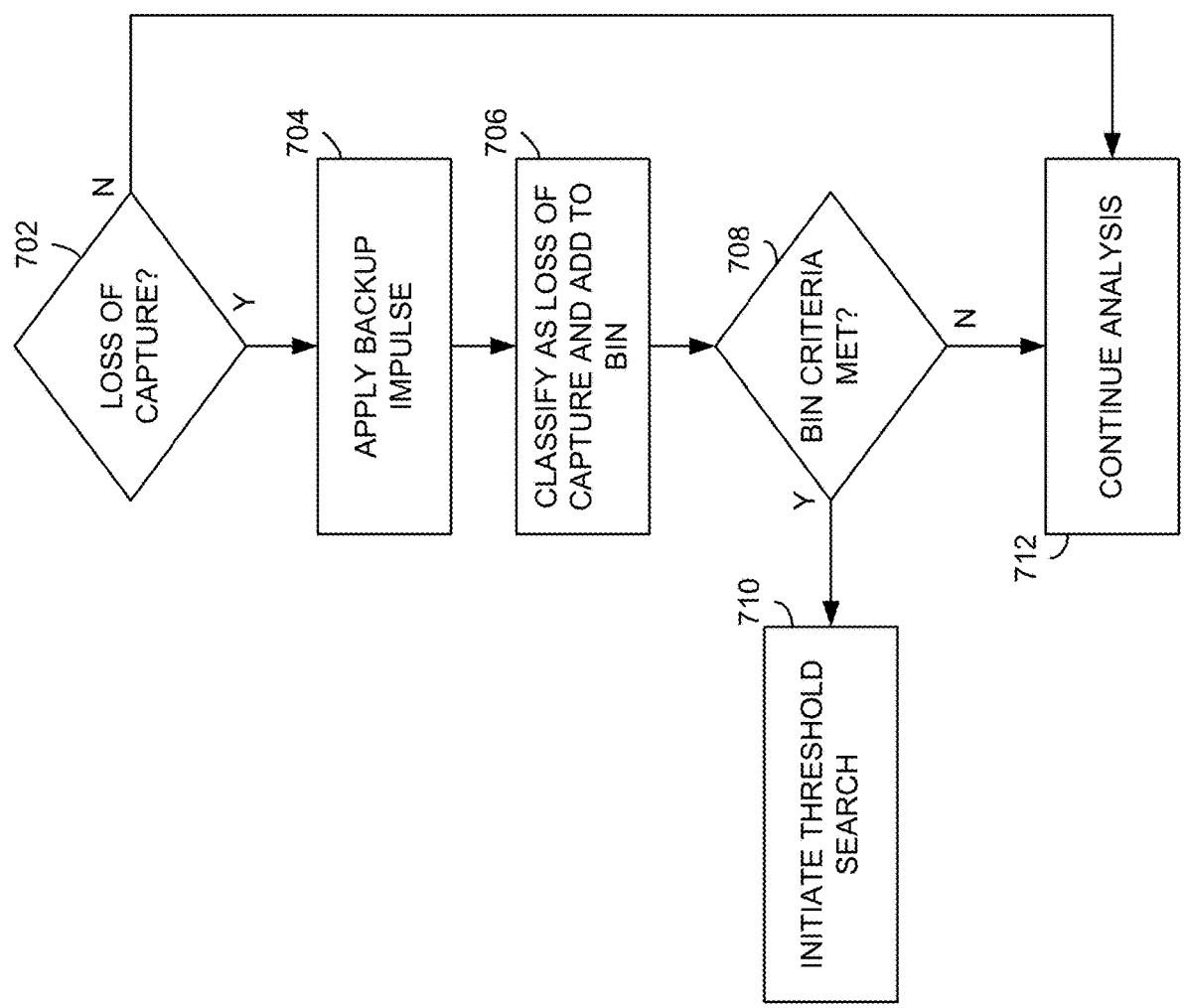
FIG. 7 is a flow chart illustrating a method for addressing loss of capture in the context of the method of FIG. 6.

FIG. 7 is a flow chart illustrating an example method 700 of identifying and processing loss of capture events. At operation 702, the stimulation device performs an initial analysis on previously obtained response data (e.g., response data obtained in operation 604 of FIG. 6). Similar to operations 606, 610, and 614 of FIG. 6, such an analysis may include identifying one or more characteristics of the response data indicative of loss of capture by comparing the response data to one or more templates or similar data stored in memory of the stimulation device.

If loss of capture has not occurred, analysis of the response data continues (operation 712). If, on the other hand, loss of capture is identified, a backup impulse is applied (operation 704), the response data is classified as indicating loss of capture and a corresponding log or "bin" entry may be generated (operation 706). In certain implementations, such an entry may simply indicate that loss of capture occurred and may provide a tally of the number of loss of capture events. In other implementations, each entry may further contain information regarding the pacing impulse (e.g., energy and duration) that may be subsequently used to perform a threshold search.

In certain implementations, a threshold search may be initiated in response to the log/bin meeting certain criteria (operation 708). Such criteria may include, among other things, the number of log/bin entries (i.e., a certain number of myocardium-only captures) being generated, a certain number of consecutive beats for which myocardium-only capture has occurred (e.g., five consecutive beats), a certain proportion of beats resulting in loss of capture (e.g., five out of the last ten beats), or any other similar criteria. As noted above, if such criteria are met, the stimulation device may initiate a threshold search (operation 710) to recalibrate the stimulation device and, in particular, the pacing impulse parameters to increase the likelihood of non-selective or selective capture. If the bin criteria are not met, the stimulation device may simply move on to continue analysis of the measured response data (operation 712). In certain implementations, the log/bin used for purposes of tracking loss of capture may be shared with a log/bin used for purposes of capturing myocardium-only capture events (e.g., the log discussed above in the context of FIG. 6). Alternatively, separate logs/bins may be maintained for each type of event. It should also be appreciated that in at least some implementations a threshold search may occur automatically in response to a single loss of capture event such that analysis of the bin criteria at operation 708 is unnecessary.

Beat-to-Beat his Bundle Pacing Using Frequency Domain Analysis

The foregoing section of the pending application was directed to systems and methods for identifying capture type based on a response to a pacing impulse delivered to the His bundle. In general, the foregoing approach included delivering the pacing impulse, measuring the response (e.g., in the form of an intracardiac electrogram (IEGM)), and analyzing various characteristics of the response as compared to templates, ranges, or similar values associated with various capture types (i.e., selective capture, non-selective capture, myocardium-only capture, and non-capture/loss of capture).

The various characteristics of the response considered in the foregoing approach for identifying capture type were in the time-domain. In other words, the particular characteristics considered were based on voltage measurements over time and included, among other things, delays between particular peaks, delays between application of the pacing impulse and features of the corresponding QRS complex, and the like. The voltage measurements further included derivatives and integrals of voltage measurements with respect to time.

In addition to or as an alternative to such time-domain analysis, implementations of the present disclosure may further take into account frequency characteristics of the IEGM (or other response) data to differentiate between types of capture. More specifically, when examined in the frequency domain, responses indicating different capture types may exhibit particular characteristics such that the response to applying a pacing impulse, when analyzed in the frequency domain, may be used to identify which type of capture has occurred.

For example, since propagation through the His bundle and associated intrinsic pathways occurs much faster than through myocardium (e.g., on the order of 4 m/s versus 0.5 m/s), the frequency response for selective capture generally exhibits greater high frequency components than the responses of either non-selective or myocardium-only capture. Accordingly, by determining the presence or amplitude of high frequency components in a response to a pacing impulse, selective capture may be distinguished from non-selective or myocardium-only capture. Similarly, non-selective capture has been experimentally shown to include a greater proportion of median frequency components as compared to myocardium-only capture.

In light of the foregoing, various frequency-based approaches may be applied to determine capture type in the context of His bundle pacing. In general, such approaches include applying a pacing impulse to the His bundle and measuring a corresponding response, such as in the form of an IEGM. In one implementation of the present disclosure, the response data is then transformed into the frequency domain (e.g., by using a fast Fourier transform or similar transformation applied to the response data). The frequency response may then be analyzed to determine what type of capture, if any, has occurred. For example and without limitation, such analysis may include determining whether certain frequencies are present in the response, the relative difference between certain frequency components, and/or the presence or amplitude of frequency components within particular frequency bands. Such characteristics of the response may then be compared to values, ranges of values, templates, or similar criteria stored in the stimulation system for each of the capture types.

Instead of immediately transforming the response data into the frequency domain, certain implementations of the present disclosure include applying one or more filters to the response to generate sets of filtered response data. The applied filters may include any of low-pass, high-pass, or band-pass filters corresponding to particular frequencies or frequency bands associated with different capture types. The resulting filtered response may then be analyzed to determine whether it indicates a particular capture type. For example, as previously noted, selective capture generally results in a response including a relatively greater proportion of high frequency components as compared to non-selective or myocardium-only capture. Accordingly, a low pass filter may be applied to the response to generate a filtered response attenuating such high frequency components. Alternatively, a high pass filter may be applied to the response to generate a filtered response isolating such high frequency components. In either case, to the extent the amplitude (or other characteristic) of the filtered response meets a particular criteria (e.g., by exhibiting frequency components above a certain frequency threshold or by having frequency components with amplitudes above an amplitude threshold), the response may be categorized as indicating selective capture. A similar approach may also be used to identify each of non-selective or myocardium-only capture. In at least one implementation, the filters may be programmed during initial testing and calibration of the stimulation device. For example, during an initial threshold (or similar) test, a technician or physician may analyze responses corresponding to the different capture types and configure one or more filters of the stimulation device based on the frequency characteristics of the responses. Alternatively, such analysis may be performed automatically by the stimulation system.

Figure 8:
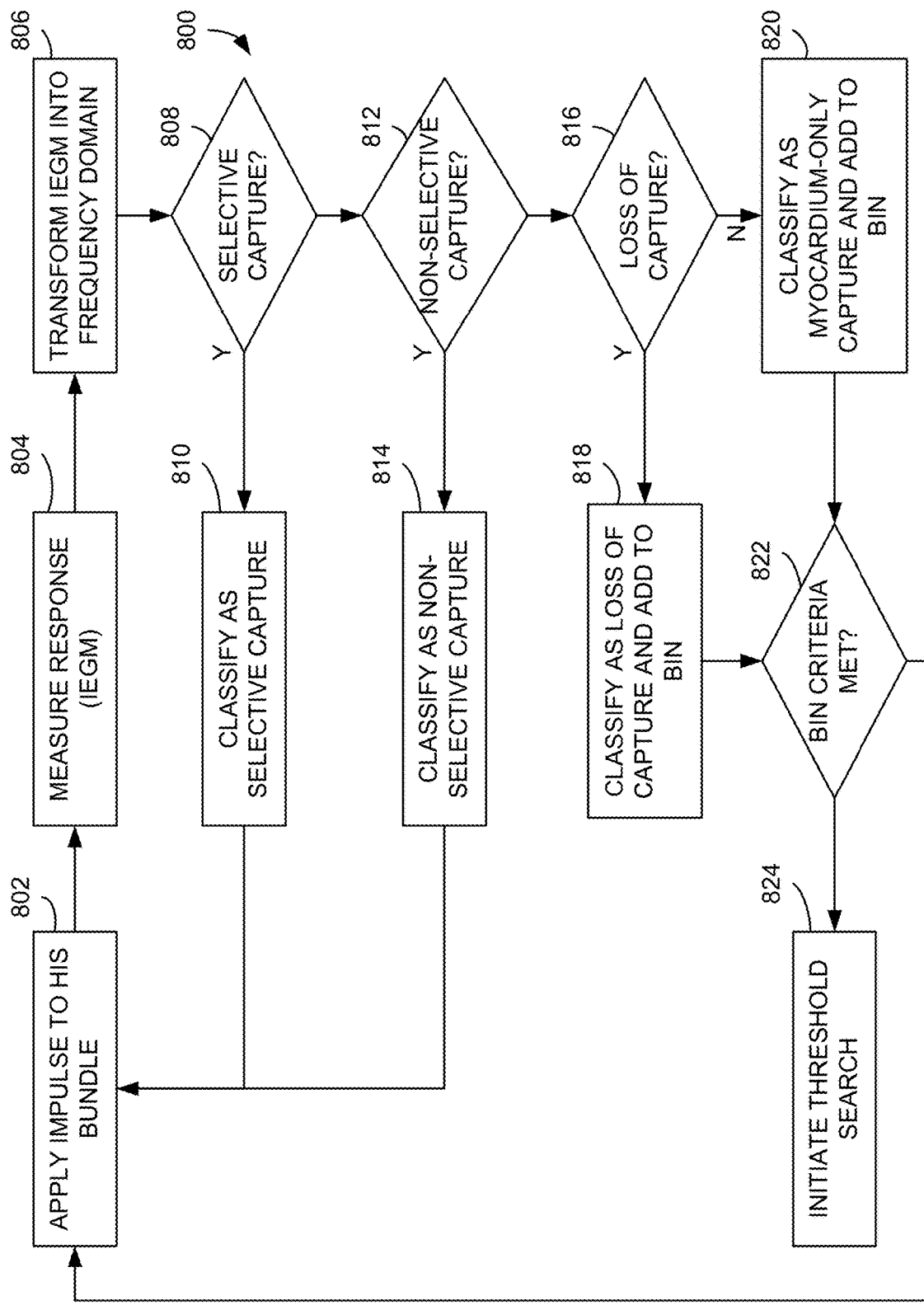
FIG. 8 is a flow chart illustrating a method for identifying capture types based on frequency spectrum characteristics of a response to a pacing impulse.
Figure 9A:
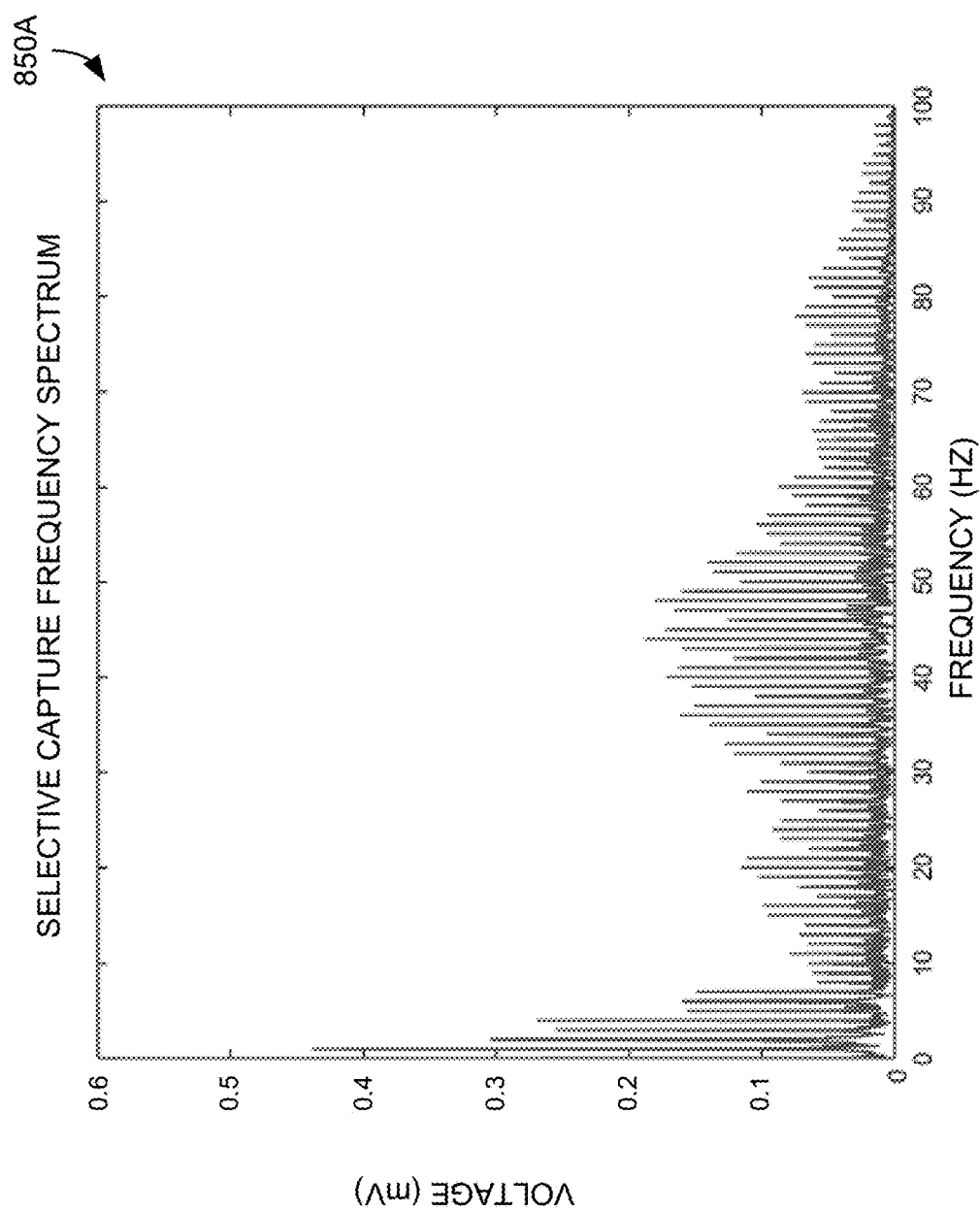
FIGS. 9A-9C are example frequency spectra for selective, non-selective, and myocardium-only capture with bipolar sensing.
Figure 9B:
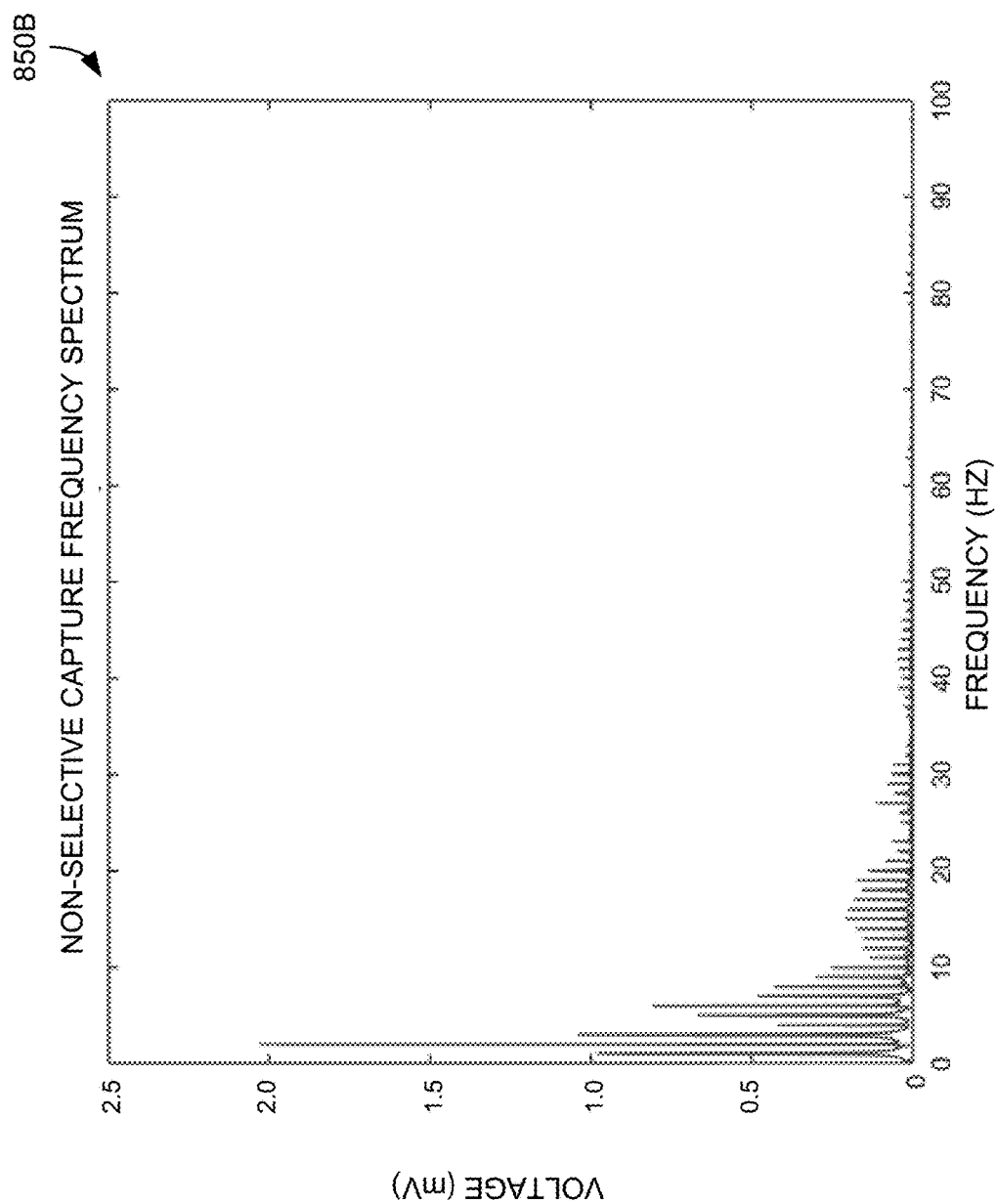
Figure 9C:
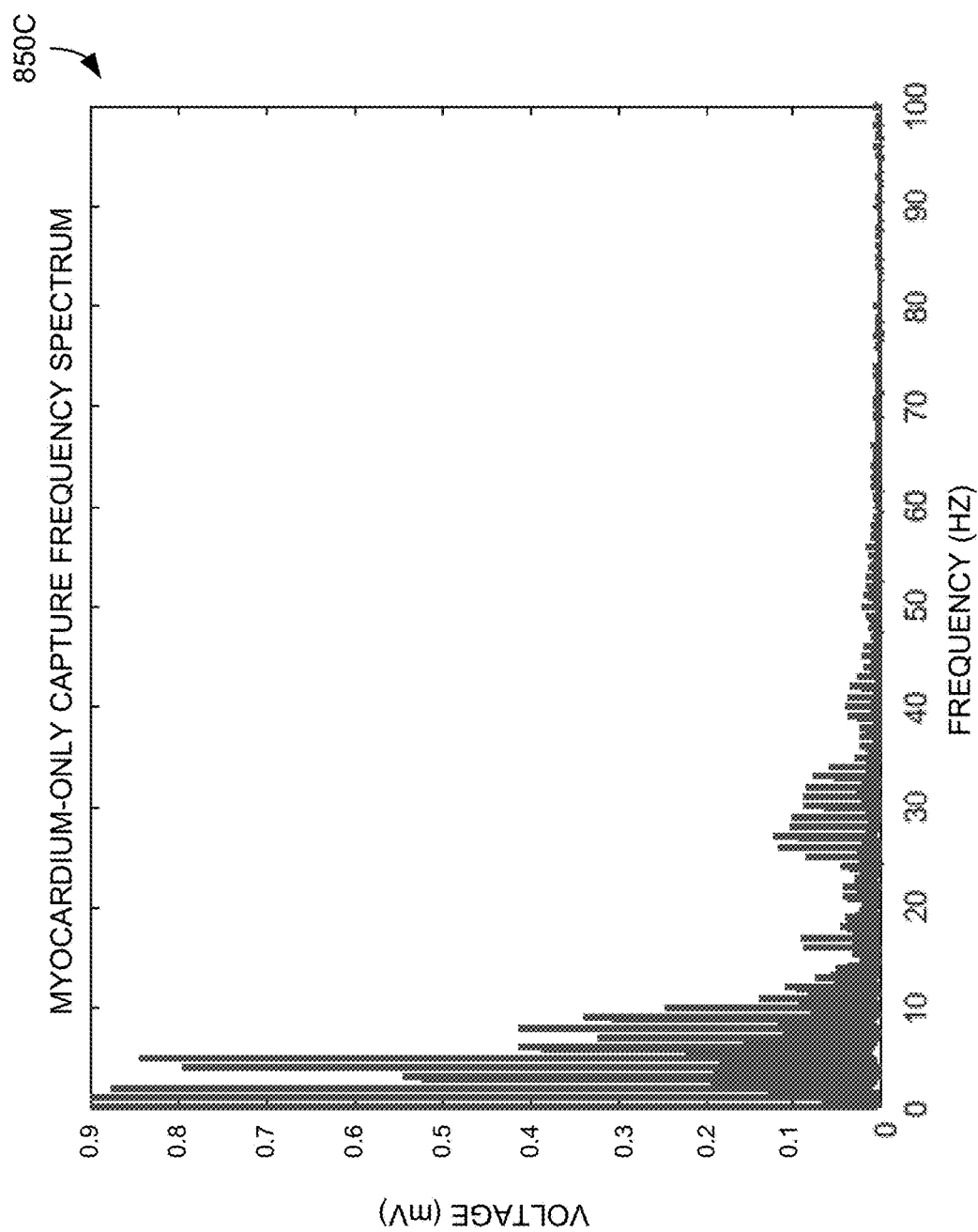

FIG. 8 is a flow chart illustrating a method 800 for performing His bundle pacing and may be executable by a stimulation system in accordance with the present disclosure. To provide additional context for the following discussion, FIGS. 9A-9C are provided, which illustrate example frequency spectra 850A-C for each of selective capture, non-selective capture, and myocardium-only capture, respectively.

In general and as described below in further detail, the method 800 includes applying a pacing impulse to the His bundle and measuring the corresponding response of the heart. The measured response is then transformed into the frequency domain to produce a frequency spectrum of the response. The stimulation system then evaluates the frequency spectrum to determine what, if any, capture has occurred. To do so, the stimulation system may compare the frequency spectrum to templates, values, ranges, or similar response characteristics for the different capture types. For example, to identify selective capture, which generally includes a high-frequency component not present in other capture types, the stimulation system may determine the amplitude and/or proportion of frequencies within the frequency spectrum.

Due to similarities in responses between different capture types, the method 800 specifically includes an elimination approach in which the measured response is first evaluated to determine whether it corresponds to selective capture. More specifically, the response is first analyzed to determine if it has characteristics indicative of selective capture only. If not, subsequent analysis is performed to determine whether the response corresponds to myocardium only or non-selective capture. As a result, the process of distinguishing between myocardium only and non-selective capture can rely on metrics for which values may overlap for selective capture. In the event of myocardium only or non-capture, the method also includes taking various remedial steps, including initiating a threshold search.

At operation 802, a stimulation/pacing impulse is applied to the His bundle and, at operation 804, the corresponding response of the heart is measured, such as by using an intracardiac electrogram (IEGM). Although operation 804 is indicated in FIG. 8 as occurring after operation 802, the stimulation system may monitoring/measure electrical activity of the heart constantly or may begin recording data prior to application of the stimulation/pacing impulse at operation 802. By doing so, the stimulation system may also measure and identify application of the pacing impulse and, as a result, may use the measured electrical activity associated with the pacing impulse when determining the type of capture.

At operation 806, the stimulation device transforms the time-based response data into a frequency response. Although various transformations may be applied to the response data, in at least one implementation of the present disclosure, a fast Fourier transform (FFT) is applied to the time-based response data to generate response data in the frequency domain. Accordingly, the time-based response (which generally indicates voltage over time) is transformed into a corresponding data set in which the time-based response is expressed as a series of sinusoids (or other periodic signals) and their respective amplitudes.

The frequency response is then analyzed to determine what type of capture, if any, has occurred in response to application of the impulse at operation 802. In one implementation, the stimulation system may analyze the frequency response data to determine whether selective capture has occurred (operation 808). To do so, the stimulation device generally analyzes the frequency response to determine if it contains high frequency components indicative of selective capture. Such analysis may be conducted in various ways; however, in one implementation (and as illustrated in the frequency spectrum 850A of FIG. 9A as compared to frequency spectra 850B and 850C of FIGS. 9B and 9C, respectively) the stimulation system may identify selective capture by determining the frequency response/frequency spectrum includes one or more components greater than approximately 30 Hz that exceed a certain threshold (e.g., 0.05 mV). In another implementation, the stimulation system may identify selective capture if average amplitude for a frequency band (e.g., 30-60 Hz) exceeds a predetermined threshold. If selective capture is detected, the stimulation device may classify the response as selective capture (operation 810) and proceed to generate an impulse for and analyze the next heartbeat (operations 802, 804).

If, on the other hand, the stimulation device determines that selective capture has not occurred, the stimulation device may further analyze the measured response to determine if it is indicative of non-selective capture (operation 812). To do so, the stimulation device may further analyze the frequency response to determine if frequency components or frequency response characteristics indicative of non-selective capture are present in the frequency spectrum. In one specific example and as illustrated by comparing the frequency spectrums of FIGS. 9B and 9C, the stimulation device analyzes a median frequency band (e.g., 10-30 Hz) and determines the signal strength within the median band. Similar to operation 808, such analysis may include, among other things, determining whether certain frequency components within the median frequency band exceed a particular threshold, determining whether the band as a whole has average amplitude above a certain threshold, identifying the presence of certain harmonics in the response data, or any other similar metric. Similar to the selective capture case, if non-selective capture is detected, the stimulation device may classify the response as non-selective capture (operation 814) and proceed to generate an impulse for and analyze the next heartbeat (operations 804, 806).

If operation 812 does result in identifying the response data as corresponding to non-selective capture, the stimulation system may next analyze the frequency response data to determine whether a loss of capture (non-capture) has occurred (operation 816). In at least some implementations, a check for loss of capture may include measuring a time between the application of the impulse at operation 802 and the onset of a corresponding QRS complex (if any) as measured in operation 804. In certain implementations, timing between application of the pacing impulse and the corresponding response may be monitored and processed separately from the response measurement of operation 804. To the extent such the delay between application of the pacing impulse and the resulting response exceeds a predetermined threshold, the stimulation system may classify the response as non-capture or loss of capture.

Similar to the method 600 of FIG. 6, when loss of capture is identified, the response may be classified as loss of capture and a log or "bin" entry may be generated indicating the occurrence of myocardium-only capture (operation 818). Alternatively, if loss of capture is not identified, the response may be classified as myocardium only capture and a corresponding bin entry may be generated (operation 820). When the entries of the log or bin meet a particular threshold (e.g., number of entries) (operation 822), a threshold search may be initiated (operation 824) to recalibrate the stimulation system. It should be understood that the test at operation 816 may instead determine whether myocardium-only capture has occurred with substantially similar results.

It should be appreciated, however, that the specific order in which the various capture type tests are applied may vary. More specifically, the stimulation device may test the response data for nay of selective capture, non-selective capture, myocardium-only capture, or loss of capture in any order. For example, loss of capture may be identified at various points during analysis and processing of response data obtained following application of the impulse to the His bundle (e.g., following operations 802-806) and is not limited to being identified immediately after conversion of the response data into the frequency domain.

For example, the test for loss of capture may occur at any point in the method 800 following application of the pacing impulse and measurement of the corresponding response (i.e., operations 802, 804). In one specific implementation, operation 816 may instead involve testing to see if myocardium-only capture has occurred. To do so, the frequency response may be further analyzed to determine if it includes substantial low-frequency components indicative of capture of the myocardium. Notably, such low-frequency components may also be present in cases of non-selective capture; however, due to the elimination of non-selective capture as a candidate in operation 1508, analysis of low frequency components of the response may be used to distinguish between myocardium-only capture and loss of capture.

In certain implementations and instead of operations 818, 822, and 824, the stimulation system may initiate a loss of capture routine in response to identifying loss of capture. Similar to previously discussed loss of capture routines, the loss of capture routine may include one or more steps directed to addressing a loss of capture event and may include, among other things, delivery of a backup impulse, generation of a bin of log entry for tracking loss of capture events, evaluation of a log or bin to determine whether a capture threshold test (or similar recalibration) is required, and initiating a capture threshold test (or similar recalibration). As previously noted, the specific details of the loss of capture routine may vary, but one example loss of capture routine is discussed in further detail above in the context of FIG. 7, albeit in the context of time-domain response data. It should be appreciated that the same routine or steps of the routine are generally applicable in the frequency-domain context as well. In other words, the general process of identifying loss of capture (operation 702) and taking subsequent remedial action (e.g., applying a backup impulse (operation 704), classifying and binning/logging the results (operations 706, 708), and initiating a threshold test if necessary (operation 710)) may be similarly applied to the frequency-domain based approach of FIG. 8, with the primary difference being that identification of loss of capture is based on analysis of a frequency spectra of the measured response.

Figure 10A:
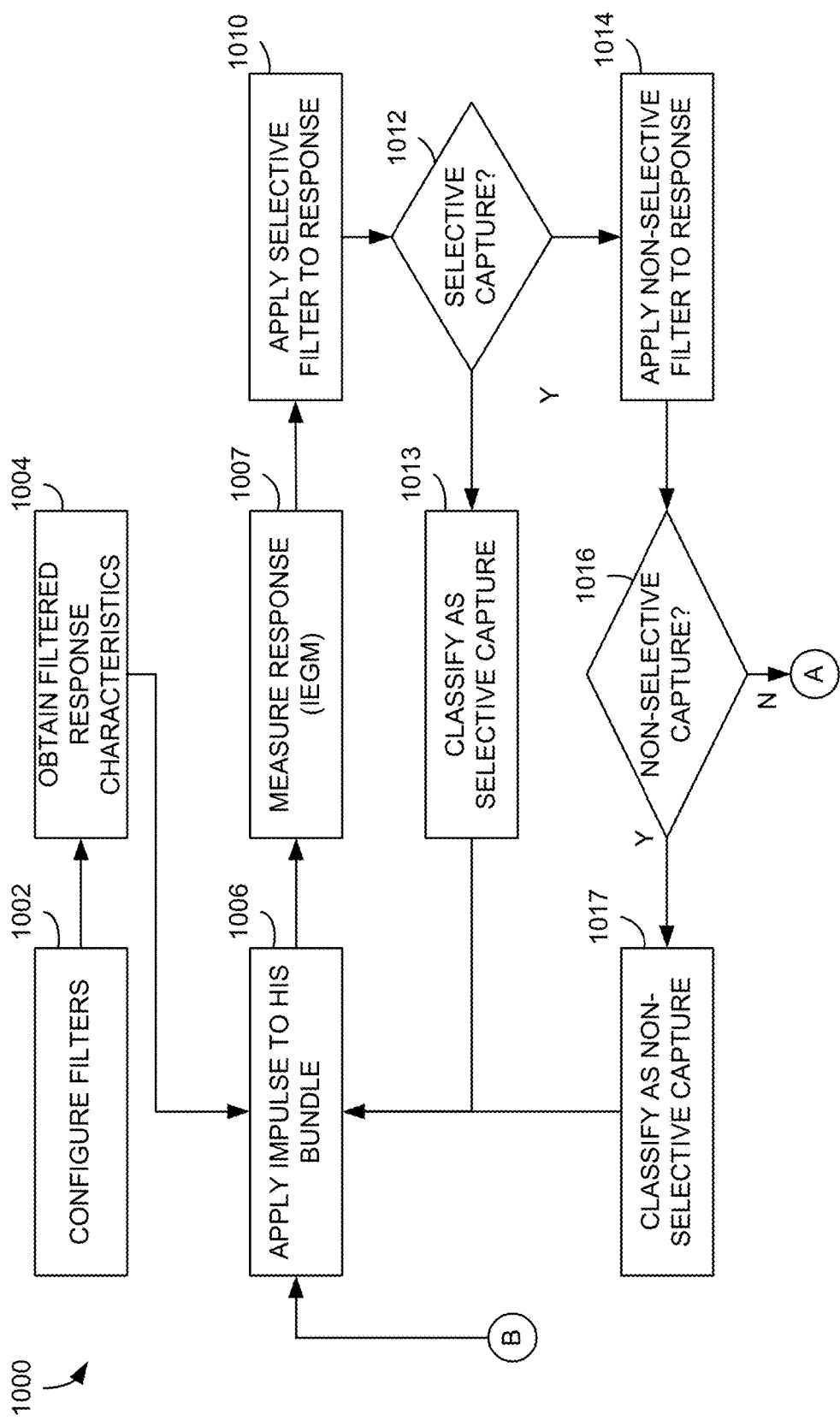

The example method 600 of FIG. 6 relies on analyzing response data using characteristics of the response data in the time-domain. In contrast, the example method 800 of FIG. 8 generally relies on transforming response data into the frequency domain and analyzing the resulting frequency response data. FIGS. 10A and 10B provide an alternative method 1000 for determining capture type that further includes the application of one or more filters to the response data to generate filtered response data. The filtered response data is then analyzed to determine what type of capture has occurred, if any.

As discussed below, the method 1000 generally includes applying a pacing impulse to the His bundle, measuring a corresponding response, filtering the response data, and analyzing the resulting filtered response data to determine whether the filtered response data is indicative of a particular capture type or excludes a capture type from consideration for the response. Notably, filtering the response data is performed independent of any subsequent analysis. As a result, analysis of the filtered response data may be conducted in either or both of the time or frequency domain, such as discussed above in the context of FIGS. 6 and 8. In general, however, one or more filters are applied to the response data to stop or pass frequencies of the response to facilitate easier discrimination between the different capture types.

At operation 1002, one or more filters of the stimulation system are configured for use in subsequent filtering of IEGM or similar response data collected following delivery of an impulse by the stimulation device. Although the exact configuration of the filters may vary in different applications of the present disclosure, configuration of the filters may generally include selecting one or more of a frequency response, a type of filter, a filter order, a stopband attenuation, and one or more cutoff frequencies. With respect to frequency response, for example, each filter may be configured as a high-pass filter, a band-pass filter, a low-pass filter, a band-stop/band-reject filter, a notch filter, a comb filter, or to have any other suitable frequency response. As another example, each filter may be further specified to be an elliptical filter, a Butterworth filter, a Chebyshev filter (type I or type II), a Bessel filter, or any other suitable filter type. In implementations in which multiple cascaded filters are implemented, configuration of the filters may also include establishing a filter order, such as by specifying inputs for each filter (which may include outputs from one or more other filters).

Configuration of the filters may occur during initial calibration and testing of the stimulation system. For example, following implantation of a stimulation device a physician or technician may conduct an initial threshold search to determine how different pacing impulses result in different capture scenarios. During such testing, IEGM or other data may be collected and analyzed to determine the particular frequency characteristics of the patient and, as a result, to determine the particular settings to be used for the filters of the stimulation device. In one specific implementation, a physician or technician may collect multiple waveforms for one or more capture types (e.g., selective capture) and analyze the waveforms in the frequency domain (e.g., by applying a FFT or similar transform to the waveform data). Based on the frequency response, the physician or technician may then determine different how best to configure the filters of the stimulation system.

In one specific example, the physician or technician may determine a cutoff frequency for identifying selective capture. As previously discussed, selective capture is generally indicated and distinguished from other capture types by the presence of relatively high frequency components. Accordingly, by observing the frequency at which such components begin in the frequency response, a physician or technician may select a cutoff frequency for a high-pass filter to pass such components for purposes of identifying the occurrence of selective capture. If the response remains strong after application of such a filter, then selective capture is likely. Alternatively, if the response is substantially attenuated, then one of non-selective or myocardium-only capture is likely. The physician or technician may alternatively select a cutoff frequency of a low pass filter to stop high frequencies indicative of selective capture. If the response is substantially attenuated by the filter, then selective capture is again likely. However, if the response remains substantially unchanged or otherwise strong, then non-selective capture or myocardium-only capture is more likely to have occurred. A similar process may be repeated for filters configured to distinguish other capture types, as discussed below in further detail.

Although described above as a substantially manual process conducted by a physician or technician, it should be appreciated that at least a portion of the filter configuration process may also be automated. For example, the stimulation system or a system configured to calibrate the stimulation system may collect response data during a threshold search or similar test and analyze the frequency responses for different capture types. Based on such analysis, the stimulation or calibration system may automatically determine some or all filter parameters to be used in identifying the different capture types. In yet another approach, filter parameters may be set in the device hardware based on previously obtained clinical data or testing data obtained during testing and development of the stimulation system.

At operation 1004, filtered response characteristics are obtained for the various capture types. In one implementation, doing so involves applying the filters configured in operation 1002 to response data for a known capture type. Characteristics and corresponding values of the resulting filtered response are then identified and stored in memory. As described below, the stored characteristics are subsequently used to analyze filtered response data to determine whether the filtered response data is indicative of a particular capture type. In general, any of the characteristics previously discussed in the context of time- or frequency-domain analysis may be used to perform any of the analyses in the method 1000 for purposes of determining capture type. For example and without limitation, if the filtered response is analyzed in the time domain, characteristics indicative of the type of capture may include: (1) waveform morphology; (2) waveform width; (3) time between stimulation and the onset of the response waveform; (4) time between stimulation and a particular peak; (5) amplitude (e.g., maximum/minimum amplitude, amplitude of a particular peak, etc.); (6) integral value of the waveform; (7) peak-to-peak slopes; and/or (8) peak-to-peak times. In certain implementations, combinations of characteristics may be stored as a template for some or all of the various capture types. If the filtered response is analyzed instead in the frequency domain, characteristics indicative of the type of capture may include, without limitation: (1) a frequency component of the frequency spectrum of the filtered response having a particular frequency; (2) a frequency component of the frequency spectrum of the filtered response being above a threshold frequency; (3) a frequency component of the frequency spectrum of the filtered response being below a threshold frequency; (4) a frequency component of the frequency spectrum of the filtered response having a minimum amplitude; (5) an average amplitude of a plurality of frequency components of the frequency spectrum of the filtered response being above or below a certain value; (6) a relative proportion of a first frequency component of the frequency spectrum of the filtered response to a second frequency component of the frequency spectrum; and/or (7) the presence of certain harmonics in the frequency spectrum of the filtered response.

Following the calibration processes of operations 1002 and 1004, the stimulation device may begin normal operation. More specifically, at operation 1006 a stimulation/pacing impulse is applied to the His bundle and, at operation 1007, the corresponding response of the heart is measured, such as by using an IEGM. Although operation 1007 is indicated in FIG. 10A as occurring after operation 1006, it should be appreciated that the stimulation system may monitor/measure electrical activity of the heart constantly or may begin recording response data prior to application of the stimulation/pacing impulse at operation 1006. By doing so, the application of the impulse may also be measured and identified and, as a result, used in determining the type of capture resulting from the application of the impulse at operation 1007.

The response measured in operation 1007 may then be filtered by applying one or more of the filters configured in operation 1002. In the method 1000, for example, a first filter is applied to the response data at operation 1010 to determine whether selective capture has occurred. Although other filters may be implemented and variation may exist between patients, in at least one implementation, the first filter may be a low pass filter having a cutoff frequency of approximately 10 Hz. Applying such a filter to a selective capture response generally results in overall greater signal attenuation as compared to applying the same filter to a non-selective or myocardium-only capture response. As another example alternative, the first filter may instead isolate frequencies that are particularly dominant in selective capture responses. For example and without limitation, in one implementation the first filter may be a band pass filter having a band from and including about 30 Hz to and including about 60 Hz. Applying such a filter to the response generates a filtered response that is generally stronger and more pronounced (e.g., having greater amplitude) than would result from the same filter being applied to a non-selective or myocardium-only capture response.

After generating the filtered response in operation 1010, the filtered response is then analyzed to determine if it is indicative of selective capture (operation 1012). As previously discussed, during calibration of the stimulation device, various characteristics for different capture types and their respective values (or ranges of values) may be identified and stored in memory of the stimulation device. Accordingly, operation 1012 generally includes identifying the same characteristics in the filtered response data and comparing the values for such characteristics to the stored characteristic data for selective capture. To the extent the characteristics of the filtered response data correspond to or match the stored characteristic data for selective capture, the stimulation system may conclude that selective capture has occurred.

In one specific and non-limiting example, the response data may be passed through a low pass filter with a cutoff frequency of 10 Hz and the resulting filtered response may be considered to be indicative of selective capture if the peak-to-peak amplitude is less than 1 mV. The stimulation device may then classify the current response as selective (operation 1013) and proceed to generate an impulse for and analyze the next heartbeat (operations 1006, 1007).

If, on the other hand, the stimulation system determines that selective capture has not occurred, the stimulation system may apply a second filter to the response data to generate a second filtered response (operation 1014). In the example method 1000, the second filter applied to the response data is specifically configured to facilitate distinction between non-selective and myocardium-only capture. For example, the second filter may be a band pass filter configured to pass median frequency components (e.g., frequency components in the 10-30 Hz range) of the response, which tend to be more prevalent for non-selective versus myocardium-only capture.

The second filtered response generated during operation 1014 may then be analyzed to determine whether it is indicative of either non-selective or myocardium-only capture (operation 1016). Similar to operation 1010, the analysis of operation 1016 may include comparison of characteristics of the second filtered response to those stored in memory of the stimulation device and corresponding to non-selective or myocardium-only capture. In one specific implementation, however, at least one of peak-to-peak slope or peak-to-peak interval of the second filtered response is used to distinguish between non-selective and myocardium-only capture. For example, peak-to-peak interval generally provides an indication of conduction velocity and is therefore greater when the intrinsic conduction pathways are recruited (e.g., during non-selective capture).

Although such values may differ in specific applications, during testing of aspects of the present disclosure, it was observed that the peak-to-peak time for filtered response data (using a 10-30 Hz band pass filter) was substantially shorter for non-selective capture (~35 ms) as compared to myocardium-only capture (~90 ms). Accordingly, in one specific implementation of the present disclosure, the stimulation system may determine whether the second filtered response indicates non-selective capture by evaluating whether the peak-to-peak time interval is less than approximately 50 ms.

The response obtained at operation 1007 may then be analyzed to determine whether a loss of capture (non-capture) has occurred (operation 1018). Identifying the response as being indicative of loss of capture may include analyzing the raw response data in the time-domain, analyzing either of the filtered responses generated in operations 1010 or 1014, or applying a third filter to the response data, the third filter configured to stop or pass specific frequencies indicative of loss of capture. If the response is identified as being indicative of loss of capture in operation 1018, the stimulation system may classify the response as loss of capture and may generate a "bin" entry, log entry, or similar record for purposes of tracking loss of capture events (operation 1020). If, on the other hand, the response is not indicative of loss of capture, the response may be classified as myocardium-only capture and a corresponding bin entry may be generated (operation 1022).

It should be appreciated that operation 1018 may instead involve testing for myocardium-only capture with substantially the same outcome. Similar to testing for loss of capture, testing for myocardium only capture may include analyzing the raw response data in the time-domain, analyzing either of the filtered responses generated in operations 1010 and 1014, or applying a third filter to the response data, the third filter configured to stop or pass specific frequencies indicative of myocardium-only capture. Similar to the previous methods when the entries of the log or bin meet a particular threshold (e.g., number of entries) (operation 1020), a threshold search may be initiated (operation 1022) to recalibrate the stimulation device.

Figure 11A:
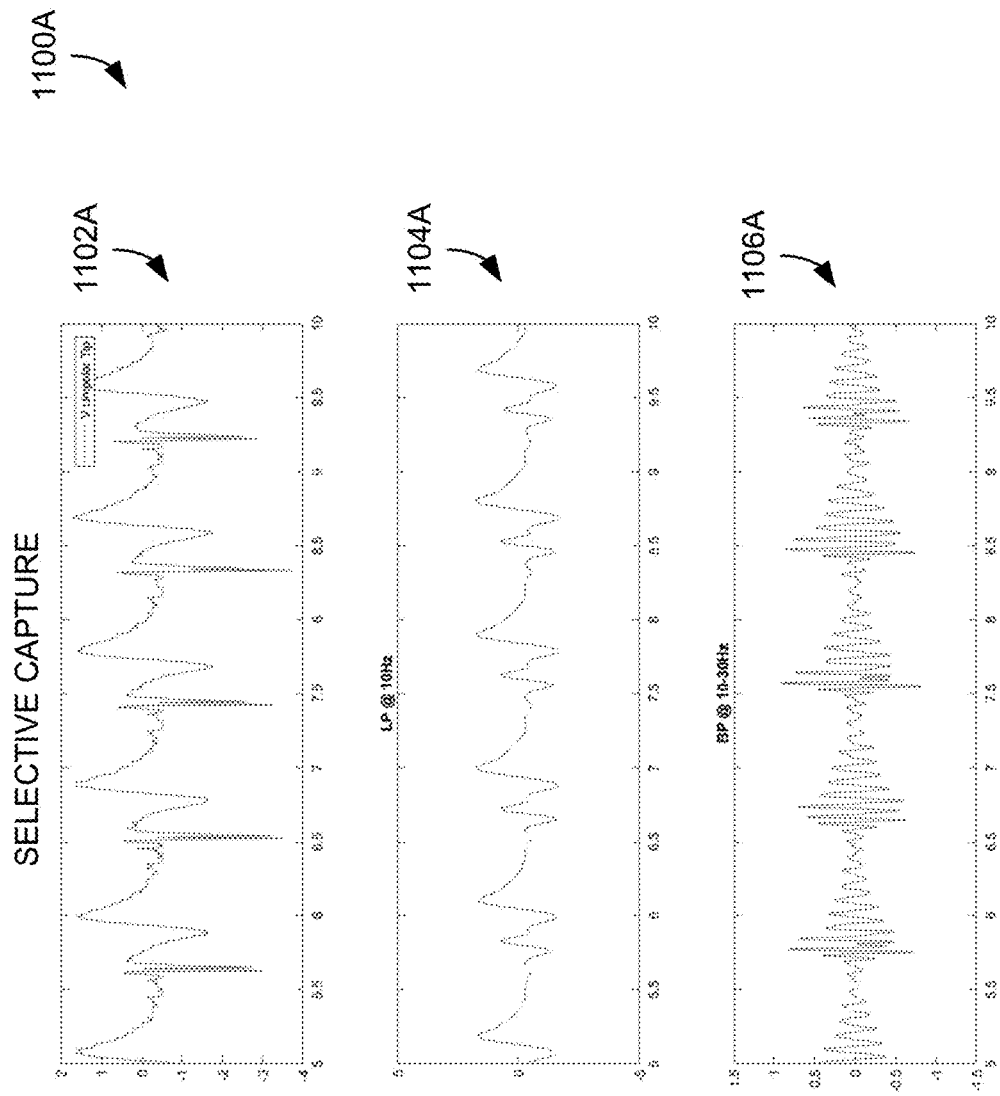
FIGS. 11A-11C are example graphs illustrating example responses (unfiltered and filtered) for selective, non-selective, and myocardium-only capture, respectively.
Figure 11B:
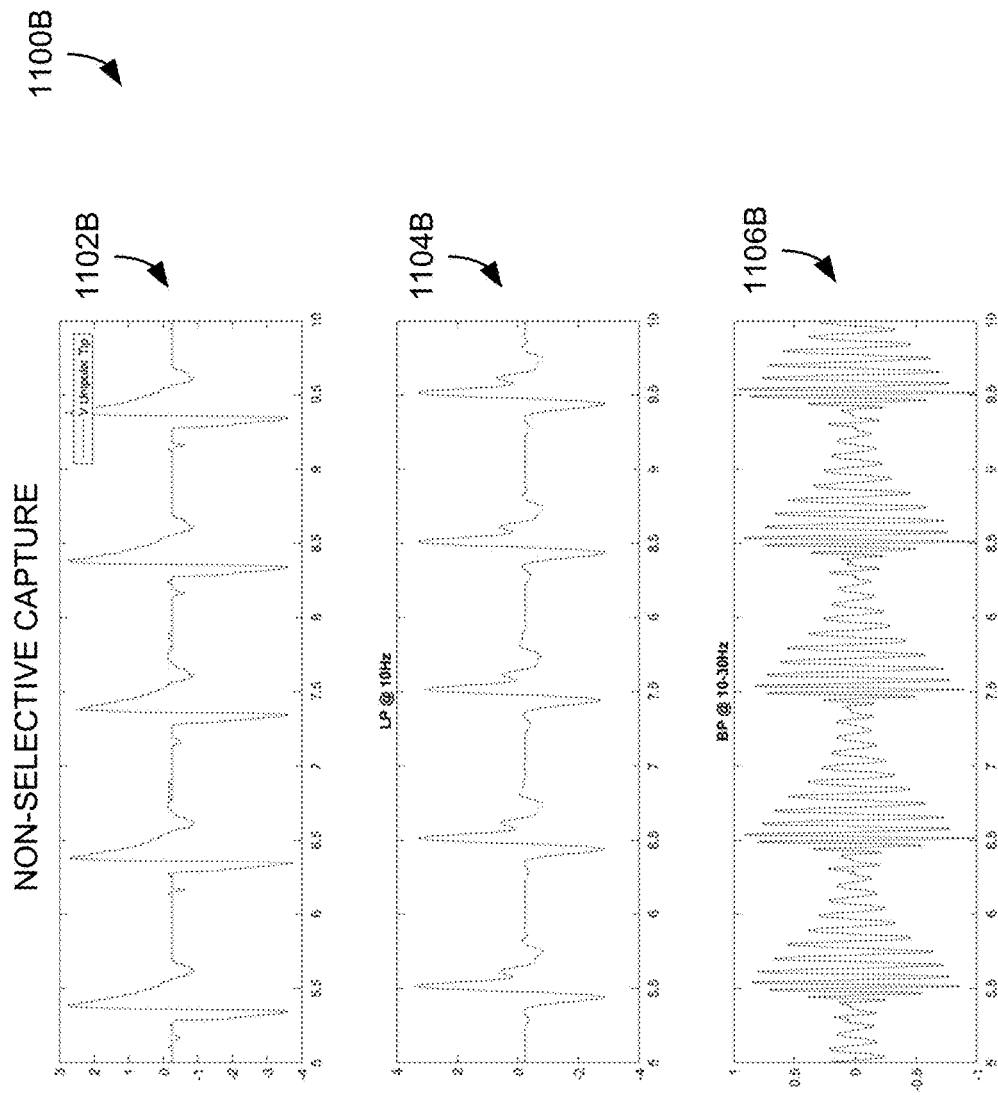
Figure 11C:
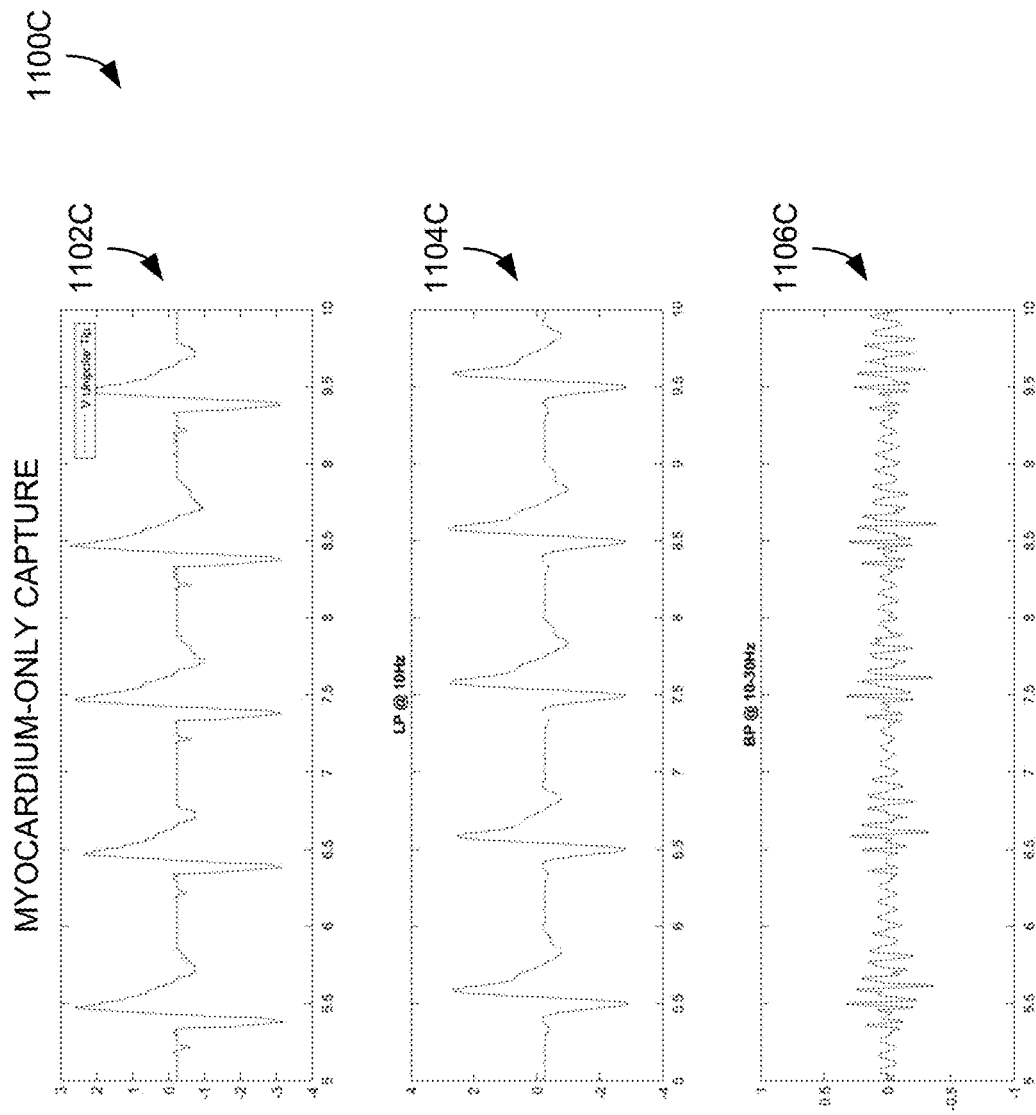

FIGS. 11A-11C are example graphs provided to illustrate the differences between responses for different types of capture when subjected to different filters and, more specifically, each of a 10 Hz low pass filter and a 10-30 Hz band pass filter. More specifically, FIG. 11A illustrates each of unfiltered 1102A, low pass filtered 1104A, and band pass filtered 1106A response data during selective capture; FIG. 11B illustrates each of unfiltered 1102B, low pass filtered 1104B, and band pass filtered 1106B response data during non-selective capture; and FIG. 11C illustrates each of unfiltered 1102C, low pass filtered 1104B, and band pass filtered 1106C response data for during myocardium only capture. Although other differences exist between the data represented in each of FIGS. 11A-11C, the response data for selective capture is distinguishable from selective and myocardium only capture at least by its relatively low amplitude when subjected to the low pass filter. Similarly, the response data for myocardium only capture is distinguishable from non-selective capture by a relatively low amplitude response when subjected to the band pass filter.

The foregoing approaches to determining capture type are applicable to both unipolar and bipolar sensing and pacing. However, in certain implementations, it may be preferable to use bipolar sensing signals for local His bundle activity.

Example Threshold Searching Approach

As previously noted, threshold searching refers to the process of identifying particular impulse characteristics at which different types of capture occur. In general, such processes include applying a pacing impulse at a starting voltage, measuring the corresponding response (e.g., by IEGM), determining what type of capture (if any) has occurred, and, based on the type of capture, modifying the voltage. The process of applying an impulse, measuring and classifying the response, and adjusting the voltage for a subsequent impulse is repeated to eventually converge on an optimal voltage setting. As described below in further detail, different approaches to setting the starting voltage, modifying the voltage, and conducting other aspects of the threshold test may be varied.

Figure 12:
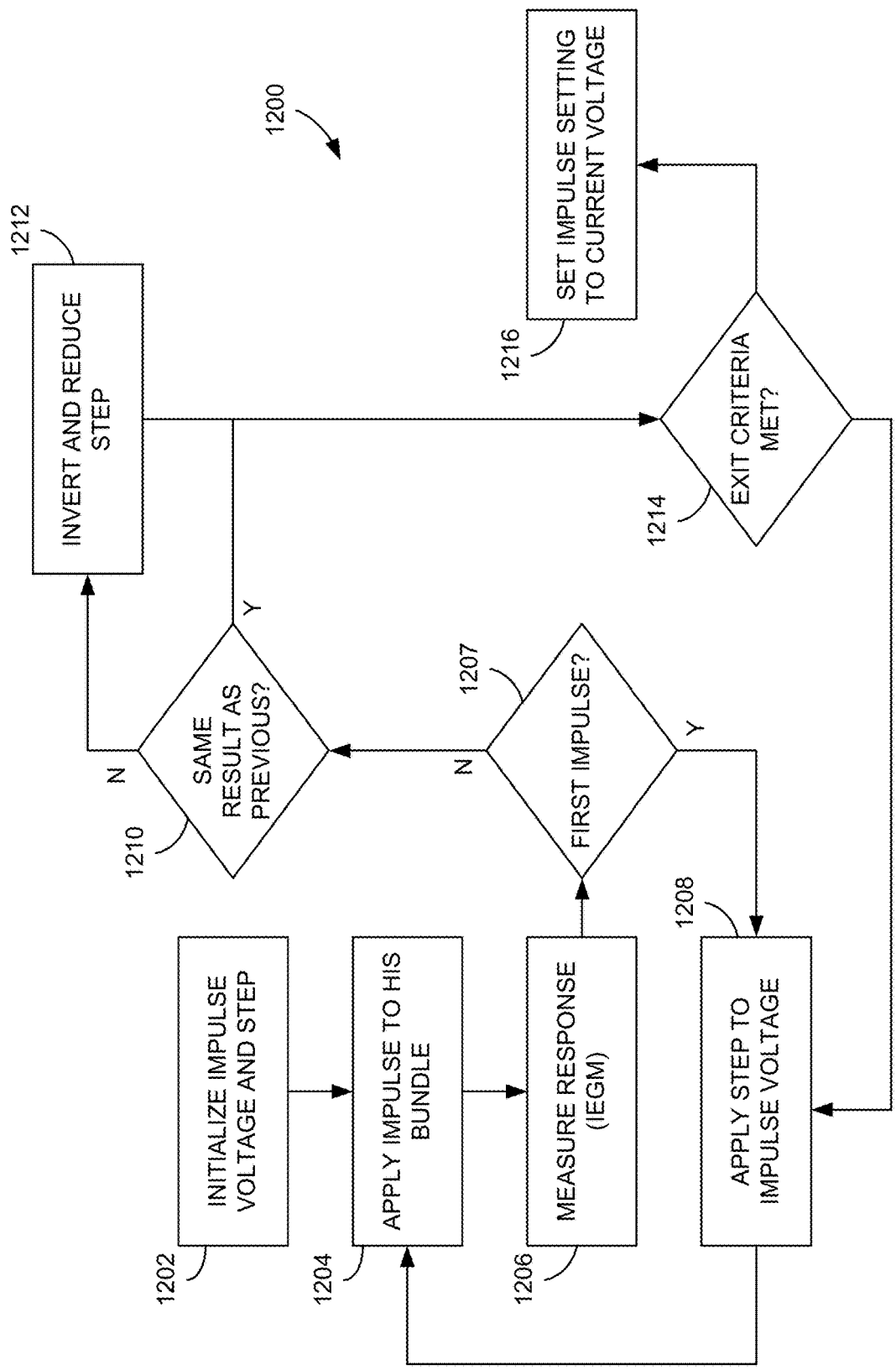
FIG. 12 is a method for performing a threshold search with a step down scheme.

FIG. 12 is a flow chart illustrating an example method 1200 for performing a threshold search. In general, the approach illustrated in FIG. 12 may be viewed as a first "step-up/step-down" approach to threshold searching. In particular, the method 1200 relies on applying a first impulse that achieves non-selective capture and reducing the voltage until capture of the His bundle is lost. The step size is then decreased and the step is inverted such that the voltage is increased until capture is regained. This process repeats with progressively smaller step sizes until a final impulse voltage is reached.

At operation 1202, the impulse voltage is set to a relatively high initial value (e.g., 5V) and a relatively large negative step size (e.g., −0.5V). At operations 1204 and 1206, a pacing impulse is delivered and the corresponding response is measured and classified to determine if the His bundle has been captured.

If the impulse applied at 1204 is the first impulse of the threshold search (operation 1207), the step is applied (operation 1208) to the impulse voltage and a subsequent iteration of applying an impulse and classifying the corresponding response (i.e., operations 1202 and 1204) is initiated.

The foregoing approach assumes that the initial impulse voltage is sufficient to capture the His bundle. However it should be appreciated that in certain implementations, capture of the His bundle using the initial impulse voltage may be confirmed from the measurements obtained during operation 1206. In the event capture does not occur, the impulse voltage may be increased until capture is achieved or the stimulation device determines capture cannot be achieved (e.g., if the devices maximum voltage is reached).

If the impulse is not the first impulse of the threshold search, the result of the current iteration and previous iteration are compared (operation 1210). If the result is the same (i.e., both of the previous and current iterations resulted in capture or non-capture of the His bundle), the step remains unchanged. However, if the previous and current iteration differ in their result (i.e., the previous iteration resulted in capture and the current iteration resulted in non-capture, or vice versa), the step is inverted and the step size is reduced (operation 1212). In one example implementation, the step size is inverted and halved (e.g., from −0.5V to +0.25V). Regardless of whether the step is modified in operation 1212 and provided one or more exit criteria are not met, the step is applied to the current impulse voltage (operation 1208) and the process of applying the impulse and evaluating the corresponding response is reiterated.

As noted, following operation 1210 (and possible adjustment of the step at operation 1212), one or more exit criteria may be evaluated (operation 1214). When the exit criteria are met, the threshold search effectively ends and an impulse voltage setting of the stimulation device is set to the current impulse voltage (operation 1216). The specific exit criteria used to trigger implemented may vary. For example, in one implementation, the exit criteria may include the step size reaching some minimum resolution. In another implementation, the exit criteria may include a predetermined number of iterations. In yet another implementation, the exit criteria may include when application of the current step would result in a previously tested value. Although illustrated as occurring after operation 1210 or 1212, it should be appreciated that the exit criteria may be evaluated at other times during execution of the method 1200.

In one specific example, suppose application of an initial 5V impulse results in non-selective capture of the His bundle. A –0.5V step is then applied such that the impulse voltage is changed to 4.5V. The subsequent 4.5V impulse again results in capture of the His bundle, so the –0.5V step is applied again. This process may be repeated until the impulse results in myocardium-only capture. For purposes of this example, it is assumed that a 3.5V impulse results in myocardium-only capture (i.e., loss of capture of the His bundle). In response to the change to myocardium-only capture, the step size is inverted and halved (i.e., set to +0.25V) and applied such that the new voltage is 3.75V. The 3.75V impulse regains non-selective capture of the His bundle, causing the step to be inverted and halved again (i.e., set to –0.125V). The step is again applied to the current impulse voltage, resulting in an impulse voltage of 3.625V. The 3.625V impulse again results in non-selective capture of the His bundle and the threshold test is concluded with a non-selective threshold of 3.625V (as applying the 0.125V step would result in the previously applied voltage of 1.5V).

The foregoing search approach can be further applied to identify thresholds for any or all types of capture associated with a patient. For example, after the non-selective capture threshold is found in the above example, the impulse voltage may be set to 3.5V (or other voltage identified as resulting in myocardium-only capture) and the step value may be reset to –0.5V. The foregoing iterative process of identifying when a change in capture type occurs, inverting and reducing the step size, and applying the new step size may then be repeated to identify the threshold between myocardium-only capture and loss of capture. By doing so, thresholds may be identified between non-selective and myocardium-only capture and between myocardium-only and loss of capture.

It should be appreciated that the foregoing approach may be inverted such that the initial voltage is set at a relatively low value to cause myocardium-only or loss of capture and increased until capture occurs. For example, suppose an initial 1.0V impulse results in capture of the myocardium only. A +0.5V step is then applied such that an impulse voltage of 1.5V is used to deliver a subsequent impulse. The 1.5V impulse again results in capture of the myocardium only, so the +0.5V step reapplied. The steps are repeated until the resulting 2.5V impulse then results in capture of the His bundle (i.e., selective or non-selective capture). In response, the step size is inverted and halved (i.e., set to –0.25V) and applied such that the new impulse voltage becomes 2.25V. The 2.25V impulse maintains capture of the His bundle and the –0.125V step is applied. The resulting 2.125V impulse results in loss of capture such that 2.125 V is identified as the threshold for selective capture.

It should be appreciated that the foregoing method may also be modified such that the threshold search is implemented as a binary search. To do so, the initial impulse value may be set without intending to specifically result in His capture or non-capture. If capture of the His bundle occurs, the sign of the step may be set to negative (i.e., the voltage of the impulse for the subsequent search iteration may be reduced). Alternatively, if non-capture occurs, the sign of the step may be set to positive (i.e., the voltage of the impulse for the subsequent search iteration may be increased). Subsequent iterations may then include reducing and inverting the step as described in the previous examples.

In one specific example of this alternative approach, the initial impulse voltage may be set to 1.5V and the initial step voltage may be 0.5V. In response to the 1.5V impulse resulting in myocardium-only capture, the impulse voltage may be increased to 2.0V (i.e., the sign of the step voltage may be set to positive). Applying the 2.0V impulse results in capture of the His bundle (i.e., selective or non-selective capture). In response, the sign of the step is inverted and the step size is reduced such that the step becomes –0.25V and the subsequent impulse becomes 1.75V. The 1.75V impulse again results in capture of the His bundle; however, instead of applying the –0.25V step (resulting in the previously tested 1.5V value), the step size is instead reduced such that the step becomes -0.125V. The subsequently applied voltage of 1.625V results in capture, and is set as the impulse voltage.

It should be appreciated that the foregoing threshold search method is provided merely as an example search method that may be used in implementations of the present disclosure. Moreover, to the extent any specific values are included in the foregoing description (e.g., for the initial voltage, initial step size, and the like), such values are included only as examples and should not be viewed as limiting.

The foregoing merely illustrates the principles of the present disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A cardiac stimulation system adapted to deliver impulses for pacing a His bundle of a patient heart using a stimulation electrode and to sense response characteristics of the His bundle and myocardium of the patient heart using one or more sensing electrodes in response to impulses delivered by the stimulation electrode, the stimulation system comprising:

a pulse generator adapted to generate electrical impulses for pacing the His bundle;

a processor communicatively coupled to the pulse generator and adapted to receive response characteristics from the one or more sensing electrodes; and a memory communicatively coupled to the processor, the memory including instructions executable by the processor that, when executed by the processor, cause the processor to:
  apply, using the pulse generator, an impulse through the stimulating electrode to induce a response from the patient heart;
  measure, using the sensing electrode, an electrical response of the patient heart to application of the impulse;
  generate response data from the electrical response of the patient heart; and
  analyze a first set of time-domain characteristics of the response, the first set of time-domain characteristics selected to determine whether the impulse resulted in selective capture of the His bundle, wherein analyzing the first set of time-domain characteristics includes applying a first filter to the response data, the first filter configured to at least one of attenuate or isolate frequencies in the response data indicative of selective capture; and
  in response to determining the impulse did not result in selective capture, the instructions further cause the processor to analyze a second set of time-domain characteristics of the response using the processor, the second set of time-domain characteristics to determine whether the impulse resulted in non-selective capture, wherein analyzing the second set of time-domain characteristics includes applying a second filter to the response data, the second filter configured to at least one of attenuate or isolate frequencies in the response data indicative of non-selective capture,
  the second set of time-domain characteristics includes at least one of:
    i) a peak-to-peak time interval, the instructions further cause the processor to determine that the impulse resulted in non-selective capture when the peak-to-peak interval is below about 60 ms; or
    ii) a time delay between application of the impulse and a last peak of the response; or
    iii) a time delay between application of the impulse and an end of a peak slope of the response.

2. The stimulation system of claim 1, wherein the first set of time-domain characteristics includes at least one of a morphology of the response, or a time delay between application of the impulse and a unipolar maximum slope of the response.

3. The stimulation system of claim 1, wherein:
the second set of time-domain characteristics includes the peak-to-peak time interval, and
the instructions further cause the processor to determine that the impulse resulted in non-selective capture when the peak-to-peak interval is below the about 60 ms.

4. The stimulation system of claim 1, wherein:
the second set of characteristics includes the time delay between application of the impulse and the last peak of the response.

5. The stimulation system of claim 4, wherein the instructions further cause the processor to determine that the impulse resulted in non-selective capture when the time delay is below about 150 ms.

6. The stimulation system of claim 1, wherein:
the second set of characteristics includes the time delay between application of the impulse and the end of the peak slope of the response.

7. A method of pacing a His bundle of a patient heart using a stimulation system, the stimulation system having a processor, a memory, a pulse generator, a stimulating electrode in proximity to the His bundle, and at least one sensing electrode adapted to sense electrical activity of the patient heart, the method comprising:
  applying, using the pulse generator, an impulse through the stimulating electrode to induce a response from the patient heart;
  measuring, using the sensing electrode, an electrical response of the patient heart to application of the impulse;
  generating response data from the electrical response;
  analyzing a first set of time-domain characteristics of the response using the processor to determine whether the impulse resulted in selective capture, wherein analyzing the first set of time-domain characteristics includes applying a first filter to the response data, the first filter configured to at least one of attenuate or isolate frequencies in the response data indicative of selective capture, and
  in response to determining the impulse did not result in selective capture, analyzing a second set of time-domain characteristics of the response using the processor to determine whether the impulse resulted in non-selective capture, wherein analyzing the second set of time-domain characteristics includes applying a second filter to the response data, the second filter configured to at least one of attenuate or isolate frequencies in the response data indicative of non-selective capture.

8. The method of claim 7, wherein the first filter is one of a low pass filter having a cutoff frequency of approximately 10 Hz and a band pass filter having a band from and including about 30 Hz to and including about 60 Hz.

9. The method of claim 7, wherein the first set of time-domain characteristics includes at least one of:
  a morphology of the response;
  a time between application of the impulse and onset of the response;
  a time between application of the impulse and a peak of the response;
  a time between application of the impulse and a unipolar maximum slope of the response;
  a width of the response;
  an amplitude of the response;
  an integral of the response;
  a peak-to-peak slope of the response; or
  a peak-to-peak time of the response.

10. The method of claim 7, wherein:
the first set of time-domain characteristics includes a time delay between application of the impulse and a unipolar maximum slope of the response, and
determining whether the impulse resulted in selective capture comprises determining whether the time delay exceeds about 70 ms.

11. The method of claim 7, wherein the second set of time-domain characteristics includes at least one of:
  a morphology of the response;
  a time between application of the impulse and onset of the response;
  a time between application of the impulse and a peak of the response;
  a time between application of the impulse and a unipolar maximum slope of the response;
  a width of the response;
  an amplitude of the response;
  an integral of the response;
  a peak-to-peak slope of the response;
  a peak-to-peak time of the response;

a time delay between application of the impulse and a last peak of the response; or a time delay between application of the impulse and an end of a peak slope of the response.

12. The method of claim 7, wherein the second set of time-domain characteristics includes a peak-to-peak time interval and determining whether the impulse resulted in non-selective capture comprises determining whether the peak-to-peak interval exceeds about 60 ms.

13. The method of claim 7, wherein the second set of time-domain characteristics includes a time delay between application of the impulse and a last peak of the response and determining whether the impulse resulted in non-selective capture comprises determining whether the time delay between application of the impulse and the last peak of the response exceeds about 150 ms.

14. The method of claim 7, wherein the second set of time-domain characteristics includes a time delay between application of the impulse and an end of a peak slope of the response and determining whether the impulse resulted in non-selective capture comprises determining whether the time delay between application of the impulse and the end of the peak slope of the response exceeds about 150 ms.

15. The method of claim 7, further comprising, in response to determining the impulse did not result in non-selective capture, classifying the response as one of myocardium-only capture or loss of capture.

16. The method of claim 15 further comprising logging each occurrence of myocardium-only capture or loss of capture in a log stored in the memory and initiating a capture threshold search in response to the log reaching a predetermined number of entries.

\* \* \* \* \*